United States Patent
Hsiao et al.

(10) Patent No.: US 12,076,694 B2
(45) Date of Patent: Sep. 3, 2024

(54) METHOD OF REMOVING PROTEIN-BOUND SUBSTANCES BY ELECTRICALLY CONDUCTIVE POLYMER

(71) Applicants: Yu-Sheng Hsiao, New Taipei (TW); Shih-Chieh Yen, New Taipei (TW); Chia-Hung Su, New Taipei (TW)

(72) Inventors: Yu-Sheng Hsiao, New Taipei (TW); Shih-Chieh Yen, New Taipei (TW); Chia-Hung Su, New Taipei (TW)

(73) Assignee: Ming Chi University of Technology, New Taipei (TW)

( * ) Notice: Subject to any disclaimer, the term of this patent is extended or adjusted under 35 U.S.C. 154(b) by 0 days.

(21) Appl. No.: 18/239,772

(22) Filed: Aug. 30, 2023

(65) Prior Publication Data

US 2023/0405532 A1    Dec. 21, 2023

Related U.S. Application Data

(63) Continuation of application No. 17/026,234, filed on Sep. 20, 2020, now abandoned.
(Continued)

(51) Int. Cl.
*B01D 71/68* (2006.01)
*A61M 1/16* (2006.01)
(Continued)

(52) U.S. Cl.
CPC ........... *B01D 71/68* (2013.01); *A61M 1/1621* (2014.02); *B01D 61/243* (2013.01); *B01D 61/30* (2013.01);
(Continued)

(58) Field of Classification Search
CPC ...... B01D 71/68; B01D 61/243; B01D 61/30; B01D 2311/2626; B01D 2311/2684; B01D 2313/345; A61M 1/1621; A61M 1/3679; C08J 3/212; C08J 2325/18; C08J 2465/00; C08J 5/2275; C08L 65/00; C08L 2203/12; C08L 2203/20; C08L 2312/08;
(Continued)

(56) References Cited

U.S. PATENT DOCUMENTS 9,890,467 B2 * 2/2018 Richardson-Burns ...................... C25D 13/20
2014/0190730 A1 * 7/2014 Frey .......................... D01F 6/44
174/257

(Continued)

OTHER PUBLICATIONS

Hakansson et al, Journal of Polymer Science, Part B: Polymer Physics 2017, 55, 814-820 (Year: 2017).*
(Continued)

*Primary Examiner* — Krishnan S Menon

(57) ABSTRACT

The present invention provides an organic bioelectronic HD device system for the effective removal of protein-bound substances, comprising PEDOT:PSS, a multiwall carbon nanotube, polyethylene oxide (PEO), and (3-glycidyloxypropyl)trimethoxysilane (GOPS). The composite nanofiber platform exhibited (i) long-term water-resistance; (ii) high adhesion strength on the PES membrane; (iii) enhanced electrical properties; and (iv) good anticoagulant ability and negligible hemolysis of red blood cells, suggesting great suitability for use in developing next-generation bioelectronic medicines for HD.

17 Claims, 14 Drawing Sheets

Related U.S. Application Data

(60) Provisional application No. 62/903,954, filed on Sep. 23, 2019.

(51) Int. Cl.
| | |
|---|---|
| *B01D 61/24* | (2006.01) |
| *B01D 61/30* | (2006.01) |
| *C08J 3/21* | (2006.01) |
| *C08L 65/00* | (2006.01) |
| *D01D 1/02* | (2006.01) |
| *D01D 5/00* | (2006.01) |
| *D01F 1/09* | (2006.01) |

(52) U.S. Cl.
CPC .............. *C08J 3/212* (2013.01); *C08L 65/00* (2013.01); *D01D 1/02* (2013.01); *D01D 5/003* (2013.01); *D01F 1/09* (2013.01); *B01D 2311/2626* (2013.01); *B01D 2311/2684* (2013.01); *B01D 2313/345* (2013.01); *C08L 2203/12* (2013.01); *C08L 2203/20* (2013.01); *C08L 2312/08* (2013.01); *D10B 2509/00* (2013.01)

(58) Field of Classification Search
CPC .. D01D 1/02; D01D 5/003; D01F 1/09; D01F 1/10; D01F 6/94; D10B 2509/00; C08K 3/041; C08G 2261/1424; C08G 2261/3223; C08G 2261/794; C08G 61/126; C09D 165/00
See application file for complete search history.

(56) References Cited

U.S. PATENT DOCUMENTS

2019/0022594 A1* 1/2019 Wang ................ B01D 67/0088
2022/0008869 A1* 1/2022 Hendren ................ B01D 71/34

OTHER PUBLICATIONS

Higgins et al, dx.doi.org/10.1021/cm203138j | Chem. Mater. 2012, 24, 828â839 (Year: 2012).*

* cited by examiner

METHOD OF REMOVING PROTEIN-BOUND SUBSTANCES BY ELECTRICALLY CONDUCTIVE POLYMER

CROSS-REFERENCE TO RELATED APPLICATION

This present application claims the benefit of, and is a continuation of, U.S. Non-provisional patent application Ser. No. 17/026,234, filed Sep. 20, 2020, entitled METHOD OF PRODUCING ELECTRICALLY CONDUCTIVE POLYMERS AND REMOVING PROTEIN-BOUND SUBSTANCES.

This application claims the benefit of U.S. Provisional Patent Application No. 62/903,954, filed on Sep. 23, 2019, entitled ELECTRICALLY CONDUCTIVE NANOFIBERS AS NOVEL ORGANIC BIOELECTRONIC INTERFACES FOR EFFICIENT REMOVAL OF PROTEIN-BOUND UREMIC TOXINS.

All of the foregoing applications are hereby incorporated by reference as if fully set forth herein in their entirety.

FIELD OF INVENTION

The present invention relates to a method of producing an electrically conductive material for blood purification; in particular, the present invention relates to a method of removing protein-bound substances by an electrically conductive polymer.

BACKGROUND OF THE INVENTION

Kidneys are organs that can filter waste metabolites from whole blood, while also regulating blood pressure and electrolyte balance. Symptoms of kidney failure result from the accumulation of uremic toxins in the blood. The rate of chronic kidney failure, causing chronic kidney disease (CKD) as well as end-stage renal disease (ESRD), is increasing rapidly worldwide. When the kidneys no longer work effectively, the concentration of uremic toxins will increase, resulting in increasing risk of mortality. Continuous ambulatory peritoneal dialysis (CAPD), hemodialysis (HD), and kidney transplantation are the three main medical treatment modalities used at present to preserve life. Although the high frequency of HD treatment (4 h each time, three times a week) is inconvenient, it remains the most viable clinical therapy and the most popular approach for the effective removal of small water-soluble uremic toxins from the blood. Nevertheless, because of their high protein-binding capacity, the removal of protein-bound uremic toxins (PBUTs) using conventional HD devices remains problematic, with only a low fraction of free-PBUTs passing through the HD membrane. Therefore, the development of new HD technologies for the removal of PBUTs from the human blood should lead to substantial improvements in the outcomes of dialysis patients.

Bioelectronic interfaces (BEIs) play key roles in communication enhancement intervention when directly interfacing biology with electronic devices. They can facilitate electrical stimulation (ES) to manipulate cellular responses (e.g., biological phenotypes and specific gene expressions) while also converting biological events to electronic signals for efficient readout. At present, most research into BEIs involves the application of organic-conjugated materials (e.g., conducting polymers (CPs), small-molecule semiconductors, and carbon materials). Relative to inorganic BEI materials, CP-based BEIs integrated with biology have a greater number of potential applications because of their extraordinary manufacturing flexibility, convenient mass production, low-temperature fabrication, intrinsic biocompatibility, biomimetic mechanical strength, and superior electrochemical and optical/photoelectric properties. Among CPs, poly(3,4-ethylenedioxythiophene) (PEDOT)-based materials have attracted the most attention for their use in bioelectronics (e.g., organic electrochemical transistors (OECTs), organic-electronic ion pumps (OEIPs), and biosensors/bioelectrodes) because they allow dynamic control over charge transport phenomenon, protein folding/conformational transitions, and capture/release modulation of circulating tumor cells through electrochemical doping/dedoping processes. Developments in multiwall carbon nanotube (MWCNT)/mixed polymer nanocomposites have been of great interest for a broad range of bioelectronic applications, due to their mechanical properties, blood compatibility, and unique electronic behavior. To the best of knowledge, there have been no previous demonstrations of robust organic BEI systems for imparting ES functions into HD treatment.

The above information disclosed in this section is only for enhancement of understanding of the background of the described technology and therefore it may contain information that does not form the prior art that is already known to a person of ordinary skill in the art.

SUMMARY OF THE INVENTION

In the present invention, MWCNT/PEDOT:PSS nanofiber mats has been developed as BEI-based HD devices for effective ES to reduce the percentage of protein binding with protein-bound substances, such as protein-bound uremic toxins (PBUTs) while preserving the retention of bovine serum albumin (BSA), thereby improving overall dialysis performance for the removal of protein-bound substances, such as PBUTs. These MWCNT/PEDOT:PSS nanofiber mats, prepared using electrospinning and thermal cross-linking, exhibited high water-resistance and strong adhesion to conventional polyethersulfone (PES) dialysis membranes. The present invention has used scanning electron microscopy (SEM), transmission electron microscopy (TEM), Raman spectrometry, X-ray photoelectron spectroscopy (XPS), a four-point probe, cyclic voltammetry (CV), and electrochemical impedance spectroscopy (EIS) to determine the nanofiber structure, chemical composition, and electrical characteristics of these MWCNT/PEDOT:PSS nanofiber mats. Furthermore, the present invention has evaluated the biocompatibility of the nanofiber mats (or device setup) in terms of the anti-thrombogenicity, hemolysis ratio, platelet adhesion, and cell viability. We have also investigated the long-term stability of MWCNT/PEDOT:PSS nanofiber-based HD devices under ES operation over the potential range from −3 to +3 V, preferably −0.8 to +0.8 V, as well as the effects of ES on the binding of PBUTs to BSA proteins.

The present invention provides a method for producing an electrically conductive polymer, comprising: (a) providing a PEDOT:PSS solution including carbon nanotubes and a crosslinking agent; and (b) blending the PEDOT:PSS solution with an additive solution to acquire a quaternary blend solution; (c) electrospinning the quaternary blend solution to form the electrically conductive polymer, wherein the additive solution is ranged 5~30 wt % based on total weight of the quaternary blend solution.

In one embodiment of the present invention, the additive solution comprises polyethylene oxide (PEO) solution, polyvinyl alcohol (PVA) solution, polyethyleneimine (PEI) solution, poly(acrylic acid) (PAA) solution, poly(styrenesulfonate) (PSS) solution, Polyvinylpyrrolidone (PVP) solution, polyacrylamide (PAM) solution, poly(ethyl exazoline) solution, poly-lysine solution, poly(propylene oxide)-poly(ethylene oxide)-poly(propylene oxide) (PPO-PEO-PPO) triblock copolymers solution, poly(ethylene oxide)-poly(propylene oxide)-poly(ethylene oxide) (PEO-PPO-PEO) triblock copolymer solution, an alginate solution, hyaluronic acid (HA) solution, a gelatin solution, a collagen solution, polyglutamic acid (PGA) solution, a chitin solution, a chitosan solution, a cellulose solution or a combination thereof.

In one embodiment of the present invention, the carbon nanotubes are ranged 1~3 wt % based on total weight of the PEDOT:PSS solution.

In one embodiment of the present invention, the cross-linking agent is (3-glycidyloxypropyl)trimethoxy silane (GOPS).

In one embodiment of the present invention, the (3-glycidyloxypropyl)trimethoxysilane (GOPS) solution is ranged 1~10 wt % based on total weight of the PEDOT:PSS solution.

Preferably, the present invention further comprises thermal treatment of the electrically conductive polymer after the step (c).

In one embodiment of the present invention, the thermal treatment is carried out under 80~150° C.

In one embodiment of the present invention, the thermal treatment is carried out at least 1 hour.

In one embodiment of the present invention, the carbon nanotubes comprise multiwall carbon nanotubes.

In one embodiment of the present invention, a ratio of PEDOT and PSS is 1:2.5~1:6.

Furthermore, the present invention offers an electrically conductive nanofiber mat produced from aforesaid electrically conductive polymer.

Also, the present invention provides a bioelectronic interface device, comprising: a dialysis membrane; a first electrode coated on the dialysis membrane; and the electrically conductive nanofiber mat described above as a second electrode coated on the dialysis membrane.

In one embodiment of the present invention, the dialysis membrane comprises polyethersulfone (PES) membrane, a cellulose triacetate (CTA) membrane, an ethylene vinyl alcohol (EVAL) membrane, a polyacrylonitrile (PAN) membrane, a polyester polymer alloy (PEPA) membrane, a polymethylmethacrylate (PMMA) membrane, a polysulfone (PS) membrane, a regenerated cellulose (RC) membrane, or a cellulose diacetate (CDA) membrane.

In one embodiment of the present invention, the first electrode is a counter electrode or a working electrode.

In one embodiment of the present invention, when the first electrode is the counter electrode, the second electrode is the working electrode; when the first electrode is working electrode, the second electrode is the counter electrode.

In one embodiment of the present invention, the first electrode comprises an Ag/AgCl electrode, a silver (Ag) electrode, a gold (Au) electrode, a platinum (Pt) electrode, an iridium (Ir) electrode, a Pt/Ir alloy electrode, an iridium oxide electrode, a titanium (Ti) electrode, or a titanium nitride (TiN) electrode.

Preferably, the bioelectronic interface device further comprises a reference electrode coated on the dialysis membrane.

In one embodiment of the present invention, the reference electrode comprises an Ag/AgCl electrode, a silver (Ag) electrode, a gold (Au) electrode, a platinum (Pt) electrode, an iridium (Ir) electrode, a Pt/Ir alloy electrode, an iridium oxide electrode, a titanium (Ti) electrode, or a titanium nitride (TiN) electrode.

In addition, the present invention imparts a method for removing protein-bound substances, comprising: (a) introducing a biological fluid sample to the aforementioned bioelectronic interface device; and (b) providing an electrical stimulation to reduce binding rate between proteins and the protein-bound substances.

In one embodiment of the present invention, the electrical stimulation comprises a cyclic voltammetric sweep.

In one embodiment of the present invention, a potential signal of the cyclic voltammetric sweep is within a voltage range from −3 to +3V.

In one embodiment of the present invention, the electrical stimulation increases retention of the protein.

In one embodiment of the present invention, the electrical stimulation increases adsorption amount or dialysis efficiency of the protein-bound substances.

In one embodiment of the present invention, the proteins dissociates from the bioelectronic interface device after the step (b).

Many of the attendant features and advantages of the present invention will become better understood with reference to the following detailed description considered in connection with the accompanying drawings.

BRIEF DESCRIPTION OF THE DRAWINGS

The embodiments will become more fully understood from the detailed description and accompanying drawings, which are given for illustration only, and thus are not limitative of the present disclosure, and wherein.

DETAILED DESCRIPTION OF THE PREFERRED EMBODIMENTS

Figure 1:
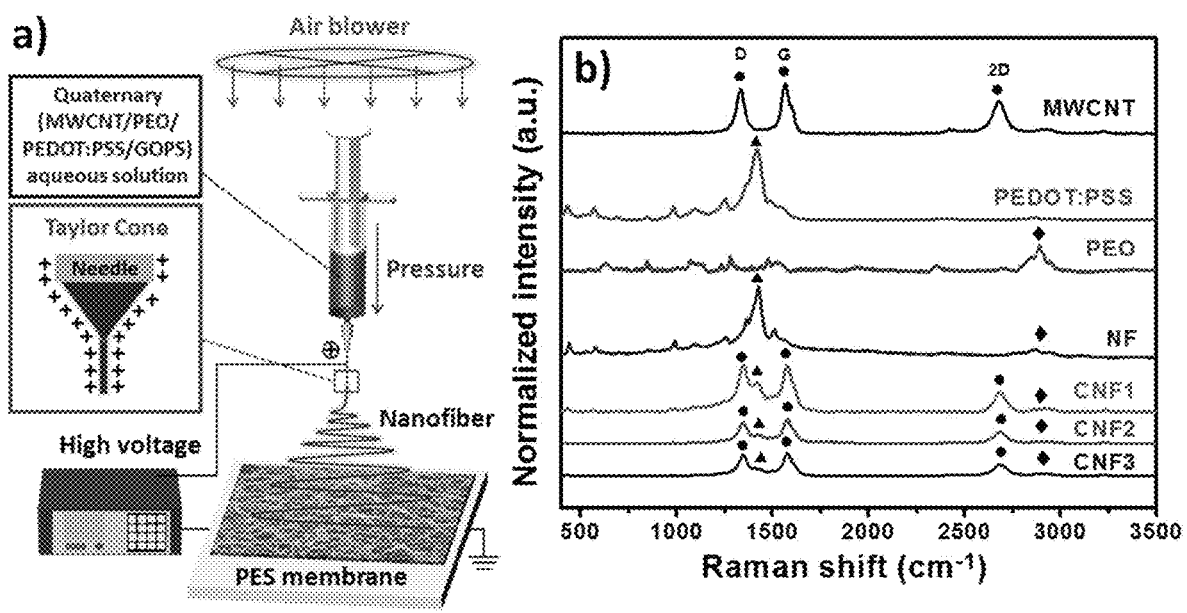
FIG. 1 (a) Schematic representation of the electrospinning setup for the fabrication of MWCNT/PEDOT:PSS nanofiber mats on a PES membrane, (b) compositional analysis of the raw materials (MWCNT, PEDOT:PSS, PEO) and MWCNT/PEDOT:PSS nanofiber mats incorporating various amounts of MWCNTs (NF, CNF1, CNF2, CNF3)

Reference will now be made in detail to the exemplary embodiments of the present invention, examples of which are illustrated in the accompanying drawings. Therefore, it is to be understood that the foregoing is illustrative of exemplary embodiments and is not to be construed as limited to the specific embodiments disclosed, and that modifications to the disclosed exemplary embodiments, as well as other exemplary embodiments, are intended to be included within the scope of the appended claims. These embodiments are provided so that this invention will be thorough and complete, and will fully convey the inventive concept to those skilled in the art.

For convenience, certain terms employed in the specification, examples and appended claims are collected here. Unless defined otherwise, all technical and scientific terms used herein have the same meaning as commonly understood by one of the ordinary skill in the art to which this invention belongs.

Various embodiments will now be described more fully with reference to the accompanying drawings, in which illustrative embodiments are shown. The inventive concept, however, may be embodied in various different forms, and should not be construed as being limited only to the illustrated embodiments. Rather, these embodiments are provided as examples, to convey the inventive concept to one skilled in the art. Accordingly, known processes, elements, and techniques are not described with respect to some of the embodiments.

The following definition is applied in all disclosure of the present invention. The weight percentage of all polymers, gels, and other materials is represented by dry weight basis. The term "polymer" means homopolymer or copolymer.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present invention and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

"Wt. %" means the number of parts by weight of monomer per 100 parts by weight of polymer, or the number of parts by weight of ingredient per 100 parts by weight of composition or material of which the ingredient forms a part.

The following descriptions are provided to elucidate the process of preparing an electrically conductive nanofiber mat for purification blood and to aid it of skilled in the art in practicing this invention. These Examples are merely exemplary embodiments and in no way to be considered to limit the scope of the invention in any manner.

Protein-bound uremic toxins (PBUTs) can cause noxious effects in patients suffering from renal failure as a result of inhibiting the transport of proteins and inducing their structural modification; they are difficult to remove through standard hemodialysis (HD) treatment. Herein, the present invention reports an organic bioelectronic HD device system for the effective removal of PBUTs through electrically triggered dissociation of protein-bound substances, such as protein-bound toxin complexes. To prepare this system, the present invention employed electrospinning to fabricate electrically conductive quaternary composite nanofiber mats—comprising multiwall carbon nanotubes (MWCNTs), poly(3,4-ethylenedioxythiophene):polystyrenesulfonate (PEDOT:PSS), poly(ethylene oxide) (PEO), and (3-glycidyloxypropyl)trimethoxysilane (GOPS)-on conventional polyethersulfone (PES) dialysis membranes. These composite nanofiber platforms exhibited (i) long-term water-resistance (due to crosslinking among PSS, PEO, and GOPS); (ii) high adhesion strength on the PES membrane (due to GOPS functioning as an adhesion promoter); (iii) enhanced electrical properties [due to the MWCNTs and PEDOT:PSS promoting effective electrical stimulation (ES) operation in devices containing bioelectronic interfaces (BEI)]; and (iv) good anticoagulant ability and negligible hemolysis of red blood cells. The present invention employed this organic BEI electronic system as a novel single-membrane HD device to study the removal efficiency of four kinds of the uremic toxins [p-cresol (PC), indoxyl sulfate (IS), and hippuric acid (HA) as PBUTs; creatinine (CRT) as a non-PBUT] as well as the effects of ES on lowering the protein binding ratio. The organic BEI devices provided a high rate of removal of PC with low protein loss after 4 h of a simulated dialysis process; it also functioned with low complement activation, low contact activation levels, and lower amounts of platelet adsorption, suggesting great suitability for use in developing next-generation bioelectronic medicines for HD.

Experimental Section

The following descriptions represent merely the exemplary embodiment of the present invention, without any intention to limit the scope of the present disclosure thereto. Various equivalent changes, alternations or modifications, based on the claims of present invention are all consequently viewed as being embraced by the scope of the present invention.

Materials and Methods

MWCNT/PEDOT:PSS Nanofiber Mats. The electrically conductive MWCNT/PEDOT:PSS nanofiber mats, prepared from a quaternary blend solution of MWCNTs, PEDOT:PSS aqueous solution, poly(ethylene oxide) (PEO) solution, and (3-glycidyloxypropyl)trimethoxysilane (GOPS), were deposited through needle-type electrospinning (FIG. 1a). The PEDOT:PSS aqueous solution (Clevios PH1000; the ratio of PEDOT and PSS is 1:2.5~1:6, preferably 1:2.5) was purchased from H. C. Starck. Poly(ethylene oxide) (PEO; molecular weight: 900,000), (3-glycidoxypropyl)trimethoxysilane (GOPS), and multiwall carbon nanotubes (MWCNTs; as-produced cathode deposit; O.D.×L: 7-15 nm×0.5-10 μm) were obtained from Sigma-Aldrich. PEO solution is ranged 5~30 wt % based on a total weight of the quaternary blend solution. It should be noted that PEO solution is merely an exemplary example in this embodiment, other water-soluble polymer solutions also can be used in the present invention, such as polyvinyl alcohol (PVA) solution, polyethyleneimine (PEI) solution, poly(acrylic acid) (PAA) solution, poly(styrenesulfonate) (PSS) solution, Polyvinylpyrrolidone (PVP) solution, polyacrylamide (PAM) solution, poly(ethyl exazoline) solution, polylysine solution, poly(propylene oxide)-poly(ethylene oxide)-poly(propylene oxide) (PPO-PEO-PPO) triblock copolymers solution, poly(ethylene oxide)-poly(propylene oxide)-poly(ethylene oxide) (PEO-PPO-PEO) triblock copolymer solution, an alginate solution, hyaluronic acid (HA) solution, a gelatin solution, a collagen solution, polyglutamic acid (PGA) solution, a chitin solution, a chitosan solution, a cellulose solution or a combination thereof. The following electrospinning parameters were applied: (a) a 27-gauge disposable needle was used as the anode for electrospinning (from the Taylor cone of polymer solutions) with a flow rate of 1 mL If and a voltage supply of 22 kV; (b) the distance between the collecting polyethersulfone (PES) dialysis membrane (EMD Millipore; molecular weight cut-off: 30 kDa) and the needle tip was 11 cm; (c) the polymer blend solutions were electrospun in an atmosphere of air for 10 min at ambient temperature under a relative humidity of less than 45%; (d) an air blower was employed to prevent the nanofibers from standing up during the whole electrospinning process. Finally, thermal cross-linking treatment (80° C.~150° C., preferably 130° C. for at least 1 h) of the MWCNT/PEDOT:PSS nanofiber mats, ensuring crosslinking of the PSS, PEO, and GOPS materials, was applied to enhance the wet-stability. It should be noted that a conventional crosslinking agent may be used in the present invention, but not limited to GOPS. The MWCNT/PEDOT:PSS nanofiber mats incorporating 0, 1, 2, 3, 4 and 5 wt % of the MWCNTs are named herein NF, CNF1, CNF2, CNF3, CNF4, and CNF5, respectively.

Characterization of Nanofiber Mats. Raman spectra in the range 400-3500 $cm^{-1}$ were recorded using a Raman spectrometer (HR800, HORIBA, Japan) and a 17-mW-output helium-neon (He—Ne) laser operated at a wavelength of 633 nm. Field-emission scanning electron microscopy (FE-SEM, JEOL JSM-6701F, Japan) images of the MWCNT/PEDOT:PSS nanofiber mats were obtained after they had been dehydrated and sputter-coated with platinum (<3 nm); the accelerating voltage was 15 kV. Transmission electron microscopy (TEM, JEOL 2010, Japan) images of the MWCNT/PEDOT:PSS nanofiber mats were obtained at 200 kV. Cross-cut adhesion tests of the MWCNT/PEDOT:PSS nanofiber mats on PES substrates were performed using a cross-cut tester (ZCC 2087, Zehntner, Switzerland) in accordance with the ASTM D3359 standard.

Blood Clotting Times, Hemolytic Assays, and Platelet Adhesion Tests. Human blood stabilized with ethylenediaminetetraacetic acid (EDTA) was collected and then centrifuged to obtain the targeted liquid biopsy. Centrifugation for 15 min at 4000 rpm was used to obtain platelet-poor plasma (PPP); centrifugation for 15 min at 1000 rpm was used to obtain platelet-rich plasma (PRP); red blood cells (RBCs) were obtained by centrifuging for min at 2000 rpm, removing the upper clear serum solution, and washing five times with 1× phosphate buffer saline (PBS). To evaluate the anti-thrombogenicity of the MWCNT/PEDOT:PSS nanofiber mat-coated PES membranes, the test samples were cut into pieces (1×1 cm$^2$), incubated in PPP (0.5 mL) at 37° C. for 1 h, and then the anti-coagulation properties were determined through a clotting assay, where the coagulation pathways were monitored in terms of Factor XII of activated partial thromboplastin time (APTT, related to the intrinsic and common pathway of coagulation) and Factor VII of prothrombin time (PT, related to the extrinsic pathway of coagulation), measured using an automated blood coagulation analyzer (CA-50, Sysmex, Japan). The positive and negative controls for clotting time measurement were tested against an untreated tissue culture polystyrene (TCPS) dish and PPP without any sample added, respectively. For hemolytic assays, the diluted RBCs were prepared by diluting (1:10) the RBC suspension with PBS. Portions of the diluted RBC suspension (0.2 mL) were then treated with 0.8 mL of DI water (as positive control) or PBS buffer (as negative control). NF and CNF1 (2 mg) were incubated in the negative-control RBC suspension (1.0 mL) at 37° C. for 2 h, followed by centrifugation for 2 min at 10,000 rpm. Finally, the supernatant was subjected to UV-Vis spectrometry (V570, Jasco, Japan) to calculate the hemolytic percentage, based on its absorbance at 540 nm. The hemolytic percentage was calculated by dividing the free hemoglobin concentration in blood by the total hemoglobin concentration of each separate sample. For the platelet adhesion tests, samples (1×1 cm$^2$) were pre-incubated in PBS buffer at 37° C. for 1 h, then transferred into as-prepared PRP (1 mL; the platelet count in PRP was adjusted to 3×10$^8$ mL using PBS buffer) and incubated at 37° C. for 2 h. The PRP was aspirated and samples washed three times with PBS buffer. Finally, for fluorescence imaging, the samples were subjected to staining process with calcein acetoxymethyl ester (calcein-AM, 4 µM) for 10 min at 37° C. Prior to SEM imaging of platelet adhesion on the PES membranes, the PRP-adhered samples were fixed with 4% paraformaldehyde for 20 min and then dehydrated in ascending grades of EtOH (25, 50, 75, and 100%; each dehydration time: 20 min) with freeze-drying.

Electrical Characterization of MWCNT/PEDOT:PSS Films and Nanofibers. The electrical conductivities of the MWCNT/PEDOT:PSS films were measured using a Keithley 2400 source meter and a four-point probe. To measure the electrical conductivity of single electrospun fibers, MWCNT/PEDOT:PSS nanofibers were first electrospun onto Au interdigitated electrodes (IDEs) prepared on a glass substrate (Dropsens: DRP-G-IDEAU10). A potentiostat/galvanostat (PGSTAT320N, Autolab, Netherlands) and a frequency response analysis (FRA) module were used to determine the resistance between the two finger electrodes of the IDEs in a two-electrode configuration. The contact resistance was subtracted from the total resistance to determine the electrical conductivity of the MWCNT/PEDOT:PSS nanofiber, according to a previously reported procedure. CV and EIS were performed using a potentiostat/galvanostat with a FRA module in a three-electrode configuration in a glass cell. A Pt wire and a Ag/AgCl electrode were used as the counter electrode (CE) and reference electrodes (RE), respectively. CV measurements were performed in PBS over the potential range from −0.8 to +0.8 V at sweep rate of 100 mV s$^{-1}$. EIS measurements were performed in PBS by applying an AC voltage (amplitude: 5 mV) in the frequency range from 10$^{-1}$ to 10$^5$ Hz. Electrokinetical analysis (Zeta potential) of MWCNT/PEDOT:PSS nanofibers was performed using a SurPASS electrokinetic analyzer (Anton Paar, Australia) with two Ag/AgCl electrodes; the measurements were performed (pH range from 2 to 9) using a streaming current method with 0.001 M KCl as the electrolyte solution; the pH was adjusted to 7.4 by adding either 0.05 M HCl or 0.05 M NaOH.

XPS Measurement. XPS spectra were recorded using a PHI 5000 VersaProbe system (ULVAC-PHI, Japan) and microfocused (100 µm, 25 W) Al Kα X-rays with a photoelectron takeoff angle of 45°. The nanofiber mats were electrospun on PES membranes for transfer into the system for direct analysis. During spectral acquisition, a dual-beam charge neutralizer (7-V Ar$^+$ beam and 1-V flooding-electron beam) was used to compensate the charge-up effect.

Simulated Dialysis Experiments. In the dialysis device, a dialysis membrane having an effective area of 3.3 cm$^2$ was designed for division between two separate internal circulation compartments; one internal circulation flow used 50 mL of the PBUT solution and the other used 50 mL of PBS buffer. The flow rates of the solution reservoir (with the uremic toxin) and PBS buffer reservoir were each 50 mL min$^{-1}$. The temperature of the circulation flow was maintained at 37° C. using a water bath; samples (1 mL) were collected from the solution and PBS reservoirs at 1-h intervals over a period of 4 h; the experiments were repeated at least three times. Prior to the dialysis experiment, a washing procedure was applied using PBS buffer at 37° C. for 3 h. The changes in the concentrations of four uremic toxins [p-cresol (PC), indoxyl sulfate (IS), hippuric acid (HA), and creatinine (CRT)] were measured (UV-Vis spectrophotometer) at 277, 278, 229, and 232 nm, respectively. The removal efficiencies of these four uremic toxins were calculated using Eq. (1):

$$\text{Removal efficiency (\%)} = \frac{C_0 - C_t}{C_0} \times 100\% \tag{1}$$

where $C_0$ and $C_t$ are the uremic toxin concentrations in the solution reservoir initially and at time t (1, 2, 3, or 4 h), respectively. The concentration of BSA was determined through a Bradford protein assay using a UV-Vis spectrophotometer with monitoring at 595 nm. The BSA retention percentage was calculated using Eq. (2):

$$\text{Retention} = \frac{C_t}{C_0} \times 100\% \text{ percentage(\%)} \tag{2}$$

where $C_0$ and $C_t$ are the BSA concentrations in the solution reservoir initially and at time t (1, 2, 3, or 4 h), respectively. For the dialysis experiment of PBUT pre-bonded BSA solution, 50 ppm of targeted uremic toxins were mixed with various amount of BSA (4, 20, and 40 g L$^{-1}$) and shaken for 24 h at 37° C. Collected samples (1 mL) were purified through centrifugation (12,000×g, 25° C., 5 min) using a Vivaspin centrifuge (Vivaspin 2, 30 kDa cutoff, GE Healthcare); the PBUTs were separated into the bottom device, thereby collecting BSA proteins from the top device. The MWCNT/PEDOT:PSS nanofiber devices were operated in a two-electrode setup consisting of a working electrode (WE; ITO glass coated with PEDOT-based nanofibers) and a CE (Ag/AgCl electrode), which was connected to the RE. CV sweeping over the potential range from −3 to +3 V, preferably −0.8 to +0.8 V (sweep rate: 100 mV s$^{-1}$) was used as ES to electrically eliminate the electrostatic bonding between the PBUT and BSA.

Cell Viability Test. The human monocytic leukemia cell line THP1 was purchased from the Bioresource Collection and Research Center (BCRC, Taiwan). Fetal bovine serum (FBS) was purchased from HyClone. RPMI 1640 growth medium were purchased from Invitrogen. THP1 cells were cultured in RPMI 1640 medium supplemented with 10% FBS and maintained at $5 \times 10^5$ cells $mL^{-1}$. THP1 cell suspensions (50 mL) in a cell culture medium ($2 \times 10^6$ cells $mL^{-1}$) were prepared and filled into the solution reservoir; the cell viabilities and cell counts were monitored during 4 h of dialysis treatment, using a Luna™ automatic cell counter (Logos Biosystems, South Korea).

Results and Discussion

Ideally, it would be useful to remove PBUTs from patients through HD, but because of their electrostatic interactions with the solute and proteins, it is difficult for them to penetrate through the dialysis membrane during standard HD treatment. The present invention has developed a novel bioelectronic device integrated with electrically conductive MWCNT/PEDOT:PSS nanofiber mats for advanced blood purification. Based on a electrospinning methodology, a quaternary blend—an aqueous solution of MWCNTs, PEDOT:PSS, PEO, and GOPS—was deposited in the form of nanofibers onto a PES dialysis membrane. PEDOT:PSS (PH1000) was demonstrated readily covered the surfaces of MWCNTs after dispersing them in an aqueous PEDOT:PSS solution and applying high-power probe ultrasonication (20 kHz, 700 W), thereby stabilizing up to 10 wt % of the dispersion of MWCNTs. Furthermore, the crosslinking reactions that occur in a ternary mixture of PEO, PEDOT:PSS, and GOPS also improve the long-term water resistance of PEO/PEDOT:PSS-based nanofibers. The present invention found that using 5~30 wt %, preferably 15 wt %, PEO solution as additives based on a total weight of the quaternary blend solution, and using 1-10 wt %, preferably 3 wt % GOPS, based on total weight of the PEDOT:PSS solution not only resulted in excellent spinnability during the electrospinning process but also provided a promising approach for enhancing the fibers' mechanical stability and adhesion to the substrate. Therefore, in the present invention, based on the above formula ratio of PEO and GOPS in PEDOT:PSS suspensions, the effect of incorporating various contents (0, 1, 2, 3, 4, 5 wt %) of MWCNTs was tested with the goal of developing suitable BEI-based HD devices for PES dialysis membranes. Because the addition of 1 wt % dimethylsulfoxide (DMSO) in MWCNT/PEDOT:PSS solutions led to poor spinnability, here the present invention investigated the electrospinning parameters, the morphologies, and the dimensional and adhesion properties of MWCNT/PEDOT:PSS nanofiber mats prepared without DMSO doping (Table 1). The priorities for the nanofiber mats to be used in HD applications were low degrees of delamination and two-dimensional (2D) thin film morphologies. The present invention found in this series of experiments that a MWCNT content of less than 3 wt % in the MWCNT/PEDOT:PSS solutions converted the morphology from a three-dimensional (3D) fiber stack to 2D mats; therefore, The present invention prepared four different samples (NF, CNF1, CNF2, CNF3) to explore all of the possibilities of using nanofiber mats as BEIs in the present invention for the development of next-generation HD devices.

TABLE 1

Electrospinning parameters, morphology, and dimensional and adhesion properties of MWCNT/PEDOT:PSS nanofibers on PES membranes.

| Sample | Flow rate (m L $h^{-1}$) | Applied voltage (kV) | Humidity (%) | Morphology | Fiber diameter [a] (d, nm) | Adhesion strength [b] (Level) |
|---|---|---|---|---|---|---|
| NF | 1 | 22 | <45 | 2D mats | 142 ± 68 | 5B |
| CNF1 | 1 | 22 | <45 | 2D mats | 157 ± 65 | 4B |
| CNF2 | 1 | 22 | <45 | 2D mats | 121 ± 60 | 3B |
| CNF3 | 1 | 22 | <45 | 2D mats | 106 ± 49 | 1B |
| CNF4 | 1.4 | 23 | <45 | 3D fiber stacks | — | N/A |
| CNF5 | 0.9 | 24 | <45 | 3D fiber stacks | — | N/A |

[a] This value was obtained from the SEM image of nanofibers (N = 50).
[b] This classification of adhesion strength was evaluated according to ASTM D3359.

Figure 2:
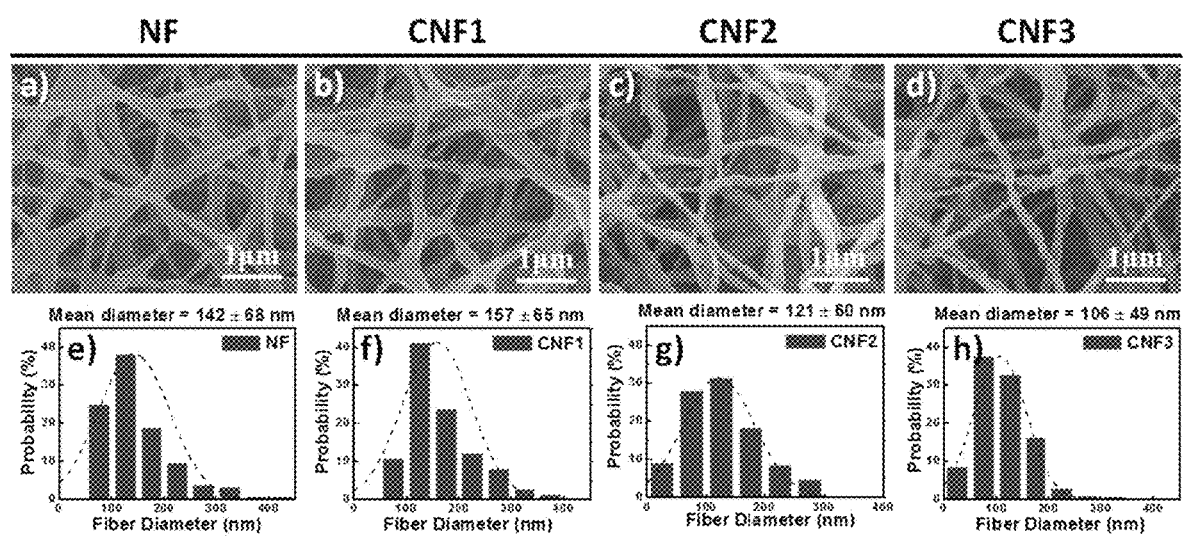
FIG. 2 (a-d) SEM morphologies of as-spun nanofiber mats incorporating various amounts of MWCNTs (NF, CNF1, CNF2, CNF3), (e-h) corresponding diameter distribution histograms of various nanofiber mats.

To examine the compositions of the electrospun MWCNT/PEDOT:PSS nanofiber mats, the Raman spectra of NF, CNF1, CNF2, and CNF3 after laser excitation was recorded at a wavelength of 633 nm (FIG. 1b). The Raman signals of the MWCNTs, corresponding the D, and 2D bands (indicated by circles), appeared at 1336, 1567, and 2683 $cm^{-1}$, respectively; the Raman signal of the PEDOT:PSS, corresponding to the ring C=C stretching vibrations for PEDOT (indicated by a triangle), appeared at 1425 $cm^{-1}$; the Raman signal of the PEO, representing C—H stretching (indicated by a rhombus), appeared at 2892 $cm^{-1}$. As expected, these characteristic signals in the spectra of NF, CNF1, CNF2, and CNF3 were consistent with their compositions of PEDOT, PEO, and MWCNTs in the electrospun nanofiber mats. Next, SEM was used to observe the morphologies of all of the MWCNT/PEDOT:PSS nanofiber mats on HD membranes; the corresponding diameter distributions were calculated through image analysis using ImageJ software (FIG. 2). The nanofibers in samples NF and CNF1 featured relatively similar diameter distributions (ca. 150 nm), whereas the nanofiber structures in CNF1 were composed of entangled MWCNTs (FIGS. 2a and 2b). When the content of MWCNTs was increased from CNF1 to CNF2 and CNF3, the nanofiber populations shifted to smaller diameters—from 157±65 nm to 121±60 and 106±49 nm, respectively—suggesting that stronger elongation forces, due to greater repulsion of charges on the PEDOT:PSS-wrapped MWCNTs at higher solid contents, were imposed upon the jet, thereby resulting in smaller fiber diameters (FIGS. 2b-d and 2f-h).

A four-point probe method has been applied to measure the electrical conductivities of all of the 2D thin film electrodes, which are presented with respect to the MWCNT contents in PEO/PEDOT:PSS solutions (FIG. 3a). 100-nm-thick BEI thin films (NF, CNF1, CNF2, CNF3) were prepared through spin-coating onto a glass substrate; the corresponding measured electrical conductivities were $3.09 \times 10^{-5}$, 0.16, 1.12, and 6.10 S $cm^{-1}$, respectively. Because of the incorporation of 11.6, 20.8, and 28.3 wt % MWCNTs in the PEO/PEDOT:PSS films, the conductivities of the CNF1, CNF2, and CNF3 thin films was approximately four, five, and six orders of magnitude higher, respectively, than that of the pristine PEO/PEDOT:PSS film (NF). In addition to the conductivity measurements using a linear arrangement of four-point probes on 2D thin films, a potentiostat/galvanostat was also used with an FRA module to measure the conductivity of one-dimensional (1D) PEDOT-based electrospun nanofibers using two finger electrodes of an inter-digitated electrodes (IDEs) setup (FIG. 3*b*), according to the previously reported procedure; the IDE measurements revealed that the 1D nanofiber structure of MWCNT/PEDOT:PSS led to a linear enhancement in the electrical conductivity upon increasing the MWCNT content, but it was one order of magnitude lower than the conductivity of the 2D thin film of the same composition.

Figure 3:
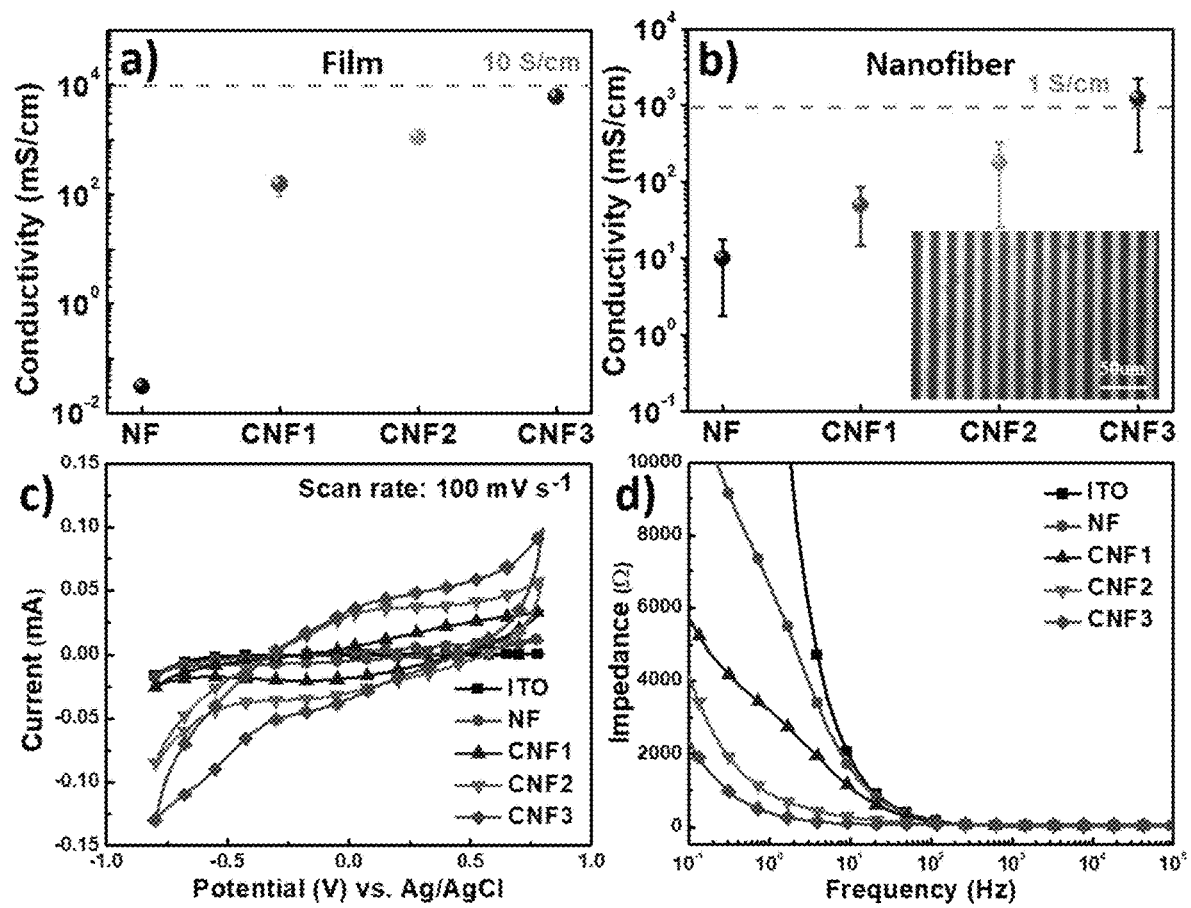
FIG. 3 (a,b) conductivities of annealed MWCNT/PEDOT:PSS incorporating various amounts of the MWCNTs in form of (a) a thin film structure and (b) a single-nanofiber structure; inset to (b): magnified optical image of electrospun MWCNT/PEDOT:PSS nanofiber mats deposited on IDEs; (c,d) Electrical properties of various MWCNT/PEDOT:PSS nanofiber mats on ITO glass in 1 PBS, (c) CV curves of NF, CNF1, CNF2, and CNF3 nanofiber mats; potential swept from −0.8 to +0.8 V at a scan rate of 100 mV s$^{-1}$; CCDs for NF, CNF1, CNF2, and CNF3 were 0.23, 0.59, 1.29, and 1.88 mC cm$^{-2}$, respectively, (d) impedance plot of EIS spectra of NF, CNF1, CNF2, and CNF3 nanofiber mats (frequency range: $10^{-1}$-$10^{5}$ Hz)

To demonstrate the device concept of using a single membrane of MWCNT/PEDOT:PSS nanofiber mats operated under ES, a standard three-electrode system and 1×PBS buffer were used to examine the CV and EIS curves of the various MWCNT/PEDOT:PSS nanofiber mats on ITO (FIGS. 3*c* and 3*d*). As displayed in FIG. 3*c*, the charge capacity density (CCD) differences of the MWCNT/PEDOT:PSS nanofiber mats NF, CNF1, CNF2, and CNF3 obtained from the CV analysis (CV sweeping voltage from −0.8 to +0.8 V) were 0.23, 0.59, 1.29, and 1.88 mC cm$^{-2}$, respectively; furthermore, the present invention found that they were more efficient at forming reduced and oxidized states to electrically eliminate the electrostatic bonding between the PBUTs and BSA, relative to the CCD of ITO electrodes (0.06 mC cm$^{-2}$). Furthermore, FIG. 3*d* presents the results of EIS analysis of all of the BEI electrodes in the frequency range from 10$^{-1}$ to 10$^5$ Hz. The EIS impedance of the MWCNT/PEDOT:PSS nanofiber mats, at frequencies below 100 Hz, decreased upon increasing the MWCNT content, indicating that a high MWCNT content in the PEO/PEDOT:PSS matrix would readily undergo a doping/de-doping process and/or cause ionic exchange in the low-frequency range of ES operation.

Figure 4:
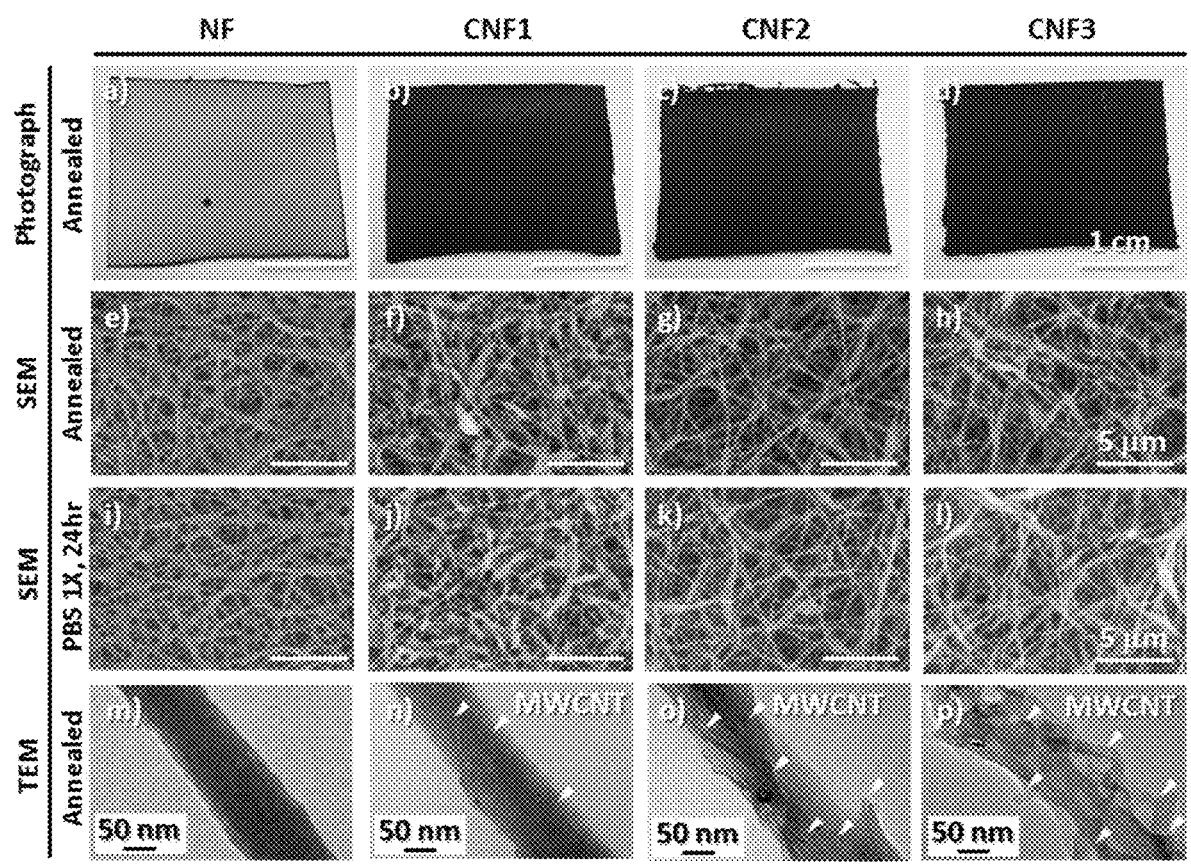
FIG. 4 (a-d) Photographs of annealed nanofiber mats incorporating various amounts of MWCNTs on PES membranes (NF, CNF1, CNF2, CNF3), (e-l) SEM morphologies of (e-h) annealed nanofiber mats (NF, CNF1, CNF2, CNF3) and (i-l) annealed nanofiber mats (with cross-linked structures) soaked in 1 PBS buffer for 24 h. (m-p) TEM images of annealed nanofiber mats (NF, CNF1, CNF2, CNF3)

Using the thermal crosslinking process that the present invention had employed previously for PEO/PEDOT:PSS nanofibers, here those thermal annealing conditions were applied to the MWCNT/PEDOT:PSS nanofiber mats deposited on the PES membranes (NF, CNF1, CNF2, CNF3) at 130° C. for 6 h, followed by PBS buffer treatment for 24 h (FIG. 4). The photographs of all of the samples in FIGS. 4*a-d* revealed a uniform coating of nanofiber mats on the PES membranes, with no apparent curling, after thermal treatment. In addition, SEM images revealed that the annealed PEDOT-based nanofibers remained intact after the long-term treatment with the PBS solution, confirming the excellent dimensional stability of the nanofibers and their water-resistance (FIGS. 4*e-l*). FIGS. 4*m-p* display TEM images revealing the different morphologies of the MWCNT/PEDOT:PSS nanofiber mats containing the various MWCNT contents. In the absence of the MWCNTs in the nanofiber mats (NF), the PEO/PEDOT:PSS formed core/shell nanofiber structures having the geometrical shapes (comprising a rough, darker, PEDOT-rich nanofiber core enclosed within a thin, brighter, PS S-rich layer). Upon increasing the content of MWCNTs, the nanofiber structures featured more MWCNTs entangled in the electrospun nanofiber and featured more pop-up structures of MWCNTs.

Figure 5:
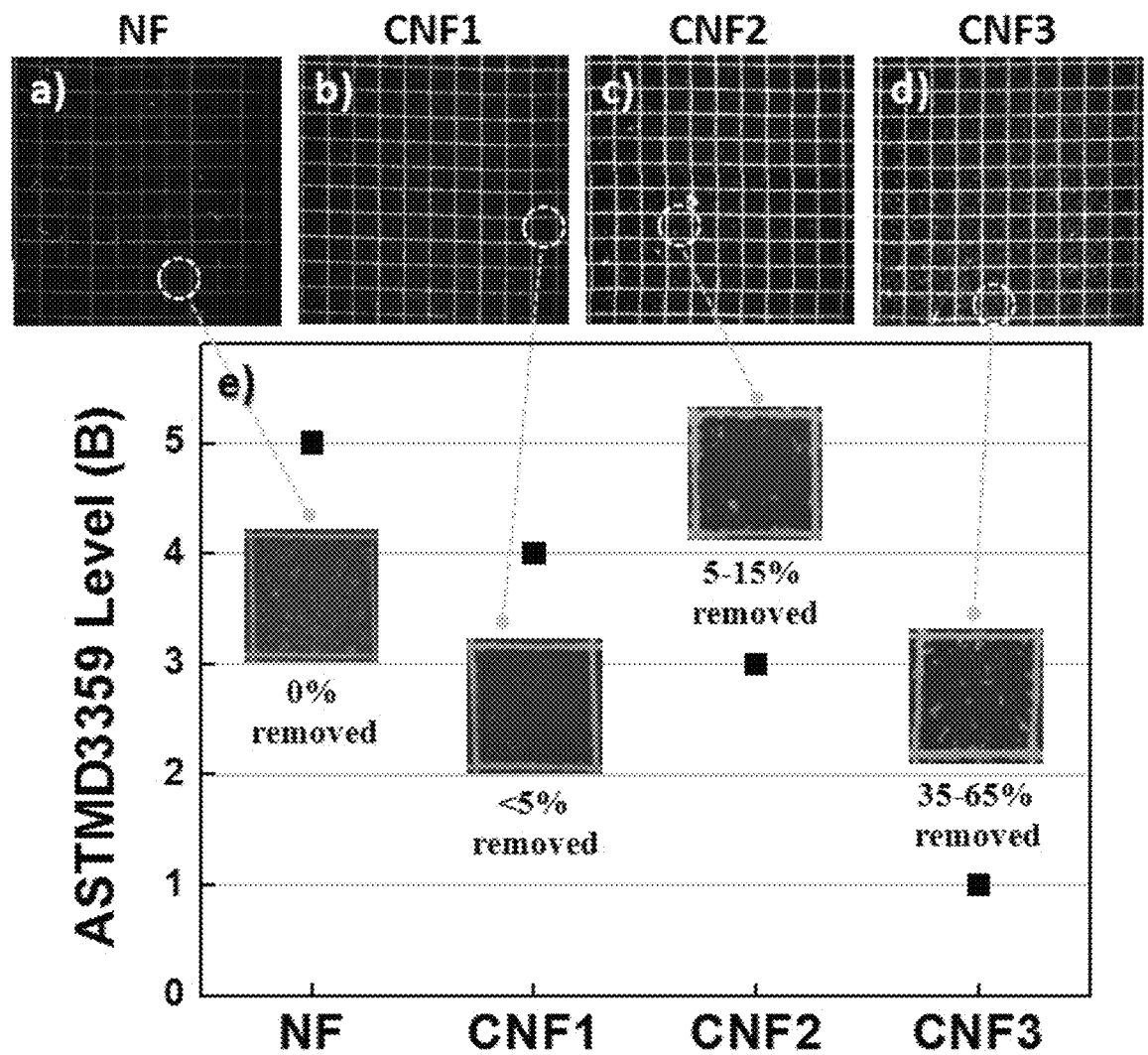
FIG. 5 (a-d) Optical images of annealed nanofiber mats on PES membranes after cross-cut tape adhesion tests of the samples NF, CNF1, CNF2, and CNF3, (e) corresponding adhesion levels (ASTM D3359) of the annealed nanofiber mats.

To evaluate the adhesion strengths of the MWCNT/PEDOT:PSS nanofiber mat coatings over the PES membranes, the present invention conducted cross-cut adhesive tape tests of the nanofiber mat-coated surfaces, using the standard American standard test method (ASTM) according to ASTM D3359 (FIG. 5). No peeling of the NF coating from the PES surface was evident under an optical microscope, suggesting that its adhesion level reached Upon increasing the content of MWCNTs, however, the adhesion level of the electrospun MWCNT/PEDOT:PSS nanofiber mat coatings worsened: from a 4B index for the CNF1 coating, down to a 3B index for the CNF2 coating and 1B index for the CNF3 coating. Indeed, the present invention found that higher contents of MWCNTs in the PEDOT:PSS matrix resulted in a much weaker bonding between the nanofiber mat and the PES membrane, thereby significantly decreasing the adhesion strength and lessening the potential for operation of HD treatment under continuous flow conditions.

Figure 6:
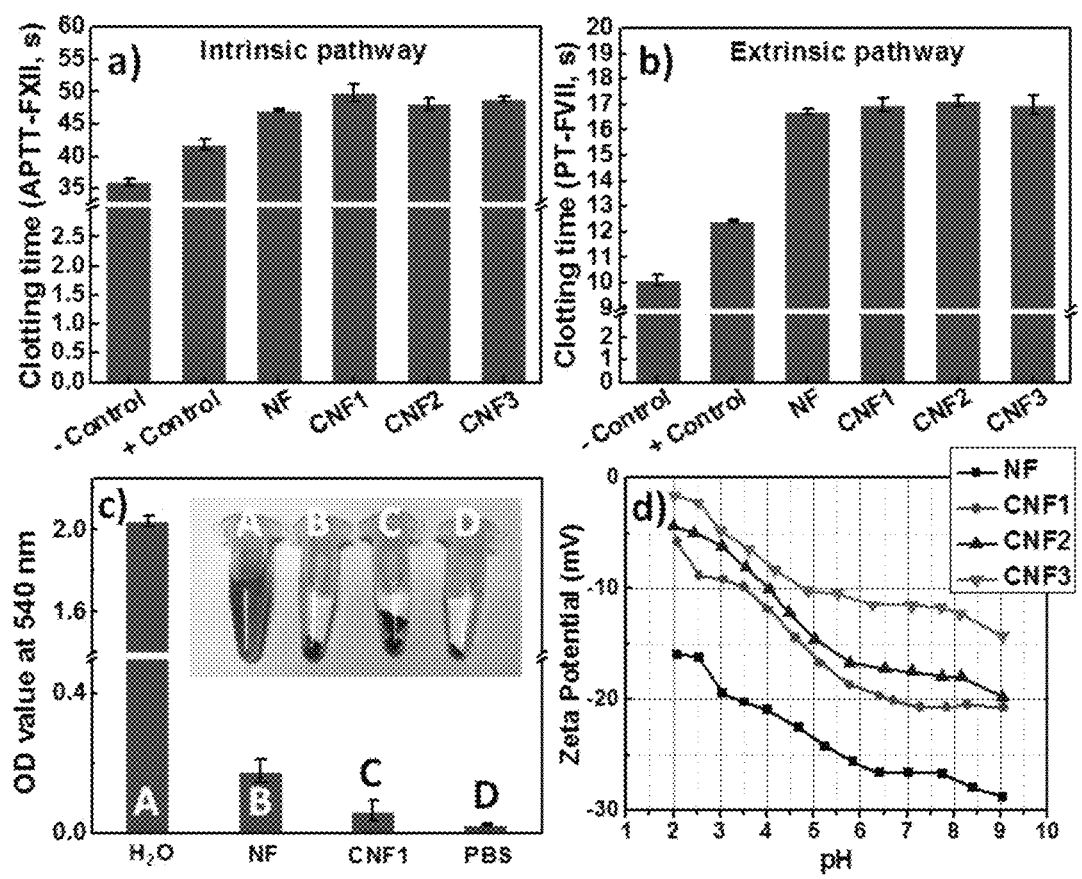
FIG. 6 (a,b) Coagulation times of annealed nanofiber mats on PES membranes (NF, CNF1, CNF2, CNF3) measured using (a) APTT, (b) PT assays, and (c) hemolysis test results of all of the nanofiber mats. Inset to (c): photograph of RBCs exposed to (A) DI water, (B) NF, (C) CNF1, and (D) 1 PBS, (d) pH-Dependence of the zeta potential of annealed nanofiber mats (NF, CNF1, CNF2, CNF3) determined using electrokinetic measurements.

As a material design concept for developing anti-coagulant membranes for advanced HD devices, the MWCNT/PEDOT:PSS nanofiber mat-coated membranes were inspired by the heparin polymer (due to the presence of sulfonic acid groups in PSS), which has been the most commonly used antithrombin-binding domain for preventing blood coagulation and thrombus formation during HD treatment. As displayed in FIGS. 6*a* and 6*b*, the present invention used the blood clotting times of APTT and PT in the intrinsic and extrinsic pathways, respectively, to evaluate the anti-thrombogenicity of NF, CNF1, CNF2, and CNF3 relative to those of the positive control of an untreated TCPS dish and the negative control of PPP without any sample added. As expected, all of PEDOT-based nanofiber mat-coated membranes provided increased blood clotting times for APTT and TT, presumably because of the sulfonic acid groups of the heparin-mimicking polymer PSS or the anti-fouling performance of the PEO domains on the nanofiber surfaces, thereby enhancing anticoagulation activity to avoid thrombus formation. CNF1 provided the largest clotting times for APTT and TT of 49.8 and 17.0 s, respectively, compared with the negative control of PPP (36.0 s for APTT; 10.1 s for TT). The present invention found that a high degree of MWCNT doping in the nanofiber mats did not have a strong influence on the clotting time, suggesting that most of the MWCNTs were covered well by a thin layer of PEDOT:PSS, as we had also observed previously for MWCNT/PEDOT:PSS scaffolds. Furthermore, the present invention confirmed the hemocompatibility of the NF and CNF1 fiber samples by using a UV-Vis spectroscopic method to quantify (FIG. 6*c*) the difference in absorbance of the supernatant at 540 nm after exposure to a suspension of RBCs, associated with the positive control (exposed to DI water to attain 100% hemolysis). When compared with the observations in the inset to FIG. 6*c*, the absence of CNF1 in the RBC suspension did not result in any obvious hemolytic effect (a hemolytic percentage of ca. 3%) when compared with the negative control (exposed to PBS), whereas the NF fiber sample caused slight hemolysis with a hemolytic percentage of less than 9%. When investigating the blood clotting and hemolytic effects of using MWCNT/PEDOT:PSS nanofiber mats, streaming potential measurements can provide information about the surface charge (zeta potential) and the isoelectric point of as-prepared samples. As displayed in FIG. 6*d*, all of the nanofiber mats (NF, CNF1, CNF2, CNF3) possessed negative zeta potentials over the wide pH range from 2 to 9. Notably, decreasing the PSS content (from 8.1% in NF to 7.1, 6.3, and 5.6% in CNF1, CNF2, and CNF3, respectively) in the PEDOT-based nanofiber structures (FIG. 3*a*) led to a slight increase in the zeta potential on the nanofiber mats at pH 7 (from −26.5 mV for NF to −20.4 mV for CNF1, −17.5 mV for CNF2, and −11.4 mV for CNF3). As these results indicate, the zeta potentials of the MWCNT/PEDOT:PSS nanofiber mats were close to that of the anticoagulant heparin (−39 mV) and the negatively charged RBCs (−17 mV), thereby providing the expected good anti-coagulant performance and hemocompatibility.

Figure 7:
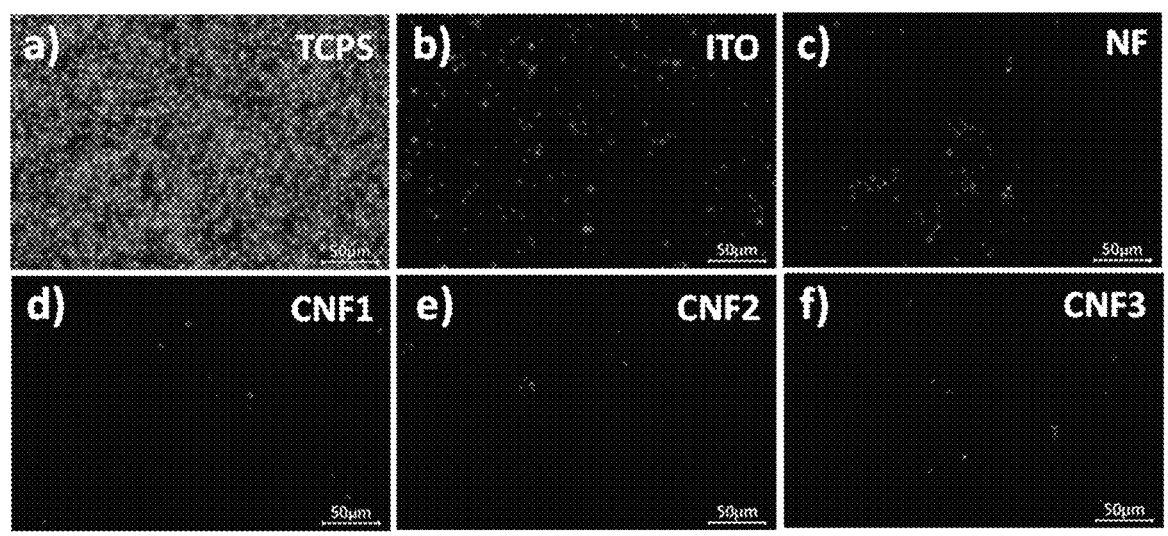
FIG. 7 (a-f) Calcein-AM-stained fluorescence images of the platelets adhered to (a) a tissue-culture polystyrene (TCPS) dish, (b) ITO glass, (c) NF, (d) CNF1, (e) CNF2, and (f) CNF3.

In addition the evaluations of blood clotting times by using the PPP test, the number of adherent platelets is another indicator that can be related to the anti-coagulant performance of PRP-adhered samples. To better visualize the small platelets (1.5-3 μm) on the opaque MWCNT/PEDOT:PSS nanofiber mats, the present invention performed calcein-AM staining to investigate the green fluorescence images of the metabolic activity of the platelets. As displayed in FIG. 7, the numbers of adhered metabolically active platelets on all of the nanofiber mats (NF, CNF1, CNF2, CNF3) were much lower than those on indium tin oxide (ITO) glass and TCPS, suggesting that the lower amount of adherent platelets would directly decrease the possibility of releasing the many clotting factors that work together in a series of complex chemical reactions, thereby reducing the risk of dialysis membrane failure arising from coagulation.

Figure 8:
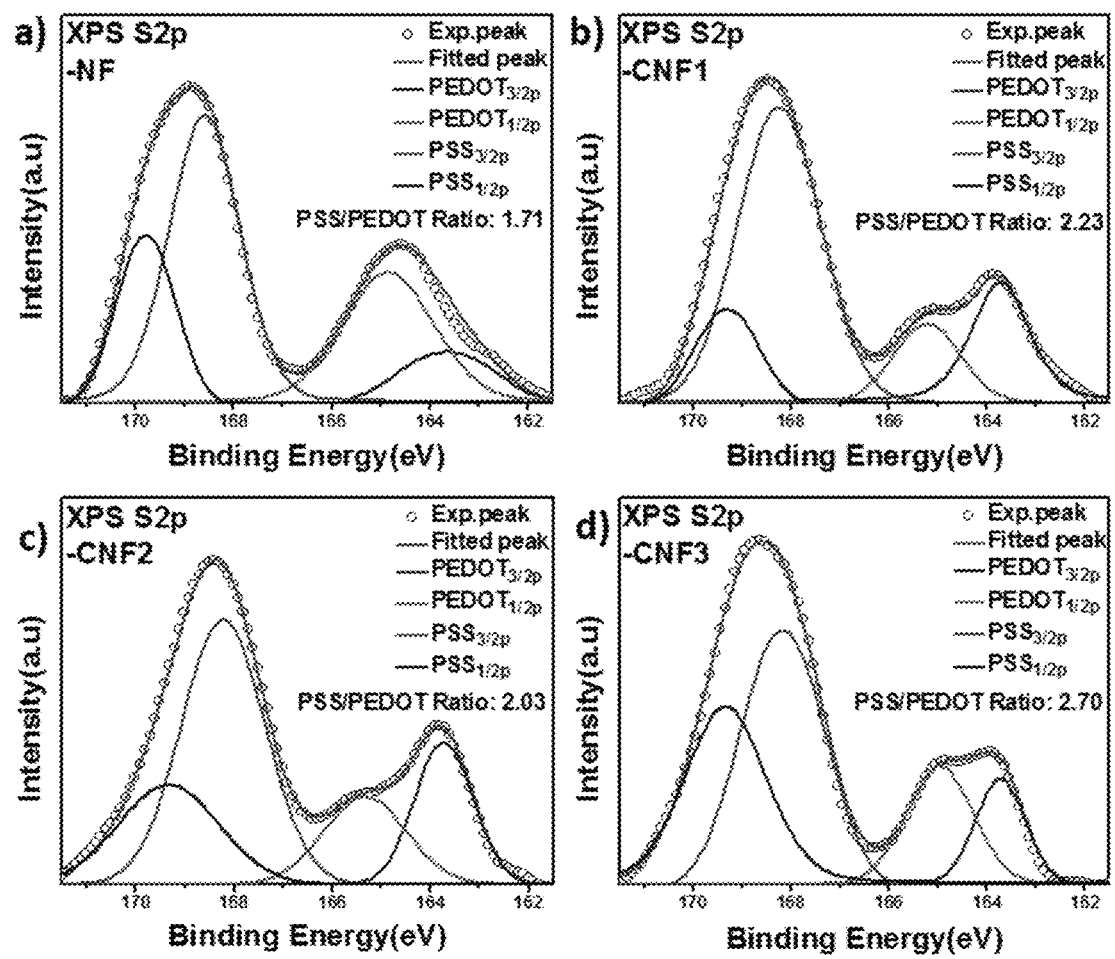
FIG. 8 XPS $S_{2p}$ spectra of annealed MWCNT/PEDOT: PSS nanofiber mats on the PES membrane. (a) NF sample, (b) CNF1 sample, (c) CNF2 sample, and (d) CNF3 sample.

To further investigate the effects of surface chemistry on the platelet morphologies on top of the PEDOT:PSS nanofiber mats, XPS was used to obtain high-resolution core-level spectra ($S_{2p}$) of NF, CNF1, CNF2, and CNF3 and then determined the changes in the PSS/PEDOT ratio in the surface composition when blending different weight percentages of MWCNTs in the PEO/PEDOT:PSS matrix, while also obtaining information about the phase separation of the PEDOT and PSS chains on the MWCNT/PEDOT:PSS nanofibers at the molecular level (FIG. 8, Table 2). Applying the same analysis method used for PEDOT:PSS materials, deconvolution of the XPS $S_{2p}$ core-level spectra allowed us to measure changes in the PSS/PEDOT composition ratio in these quaternary composite nanofiber systems. From the comprehensive assessment of PSS and PEDOT chains (with the corresponding set of S $2p_{3/2}$ and S $2p_{1/2}$ peaks), the PSS/PEDOT ratio of 1.71 for the NF increased dramatically to 2.23, 2.03, and 2.70 for CNF1, CNF2, and CNF3, respectively, signifying that some of heparin-like PSS polymers had been phase-separated to the surface of the nanofibers, thereby leading to a significant decrease in the degree of platelet adhesion.

TABLE 2

The atomic percentages of PSS and PEDOT and PSS/PEDOT ratios (from peak deconvolution of XPS $S_{2p}$ data) of MWCNT/PEDOT:PSS nanofiber mats.

| Sample | At. % from XPS ($S_{2p}$) data | | | | PSS/PEDOT ratio |
|---|---|---|---|---|---|
| | PSS $2p_{1/2}$ | PSS $2p_{3/2}$ | PEDOT $2p_{1/2}$ | PEDOT $2p_{3/2}$ | |
| NF | 19 | 46 | 27 | 8 | 1.71 |
| CNF1 | 12 | 57 | 12 | 19 | 2.23 |
| CNF2 | 21 | 46 | 15 | 18 | 2.03 |
| CNF3 | 33 | 40 | 16 | 11 | 2.70 |

Figure 9:
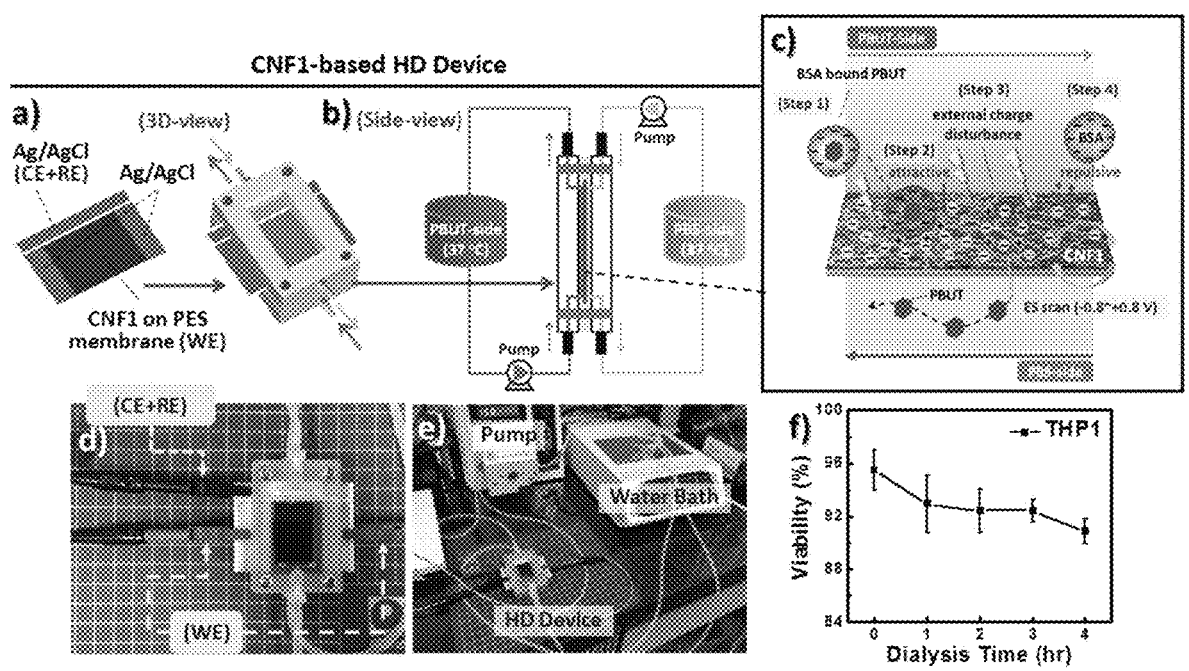
FIG. 9 (a,b) Schematic representations of the CNF1-based HD device system for simulated dialysis treatment: (a) Device architecture for single-membrane CNF1-based HD device; (b) experimental setup for dialysis treatment, where the device was connected through a peristaltic pump to control the flow rate of PBUT-side and PBS-side buffers; all reservoirs were maintained in a water bath at 37° C. (c) Concept of CNF1-based HD device for the removal of PBUTs under ES operation. (d,e) Photographs of (d) the CNF1-based HD device and (e) the experimental setup for dialysis treatment. (f) Cell viability of THP1 cells during 4 h of ES operation using CNF1-based HD devices (N=3)

Taking together the electrical properties, the adhesion strengths, the anticoagulant abilities, and the hemocompatibility, the present invention concluded that the CNF1 mats over the PES membranes exhibited the optimized performance for subsequent use in HD applications. In this proof-of-concept embodiment, the present invention first deposited the CNF1 mats and Ag/AgCl electrodes (Ag/AgCl Ink, ALS) over a PES membrane (molecular weight cut-off: 30 kDa) to form a CNF1-based HD device, and then assembled this membrane filter into a lab-scale single-membrane dialysis system (FIG. 9a), where the dialysis membrane with an effective area of 3.3 cm² was designed to be divided between two separate internal circulation compartments. As displayed in FIG. 9b, one internal circulation flow was pumped from a reservoir containing 50 mL of the specific PBUT solution (denoted as PBUT-side buffer) and passed through the left-hand side of the membrane filter (green line); another internal circulation flow was pumped from another reservoir containing 50 mL of PBS buffer solution (denoted as PBS-side buffer) and passed through the right-hand side of the membrane filter (yellow line); the flow rates of all solutions were kept at 50 mL min$^{-1}$ by using alternate opposite flow directions across the dialysis membrane. PEDOT:PSS conductive polymers exhibit promising properties as pseudocapacitor materials, meaning that charge transfer, enhanced adsorption, pH changes, and redox reactions can be facilitated near the surfaces of PEDOT:PSS nanofibers in the electrolyte. Because of the possible electrostatic interactions between the PBUTs and proteins, the present invention wanted to leverage such PEDOT:PSS behavior, using CNF1, to enhance the rejection rate of BSA and decrease the protein-bound fraction of the PBUTs under ES operation, which may feature four sequential steps: Step 1—the BSA-bound PBUT exhibits a negative charge at pH 7.4 and disperses in the PBUT-side; Step 2—the CNF1 device provides an electrostatic attractive force to promote the adsorption of net negatively charged BSA proteins on the surface under the ES operation (between 0 and 3 V, preferably between 0 and +0.8 V); Step 3—the CNF1 device electrically eliminates the electrostatic bonding between the PBUT and BSA upon CV sweeping (between −3 and +3 V, preferably between −0.8 and +0.8 V), thereby improving the clearance rate of the PBUTs; Step 4—the CNF1 device provides an electrostatic repulsion force to increase BSA retention in the PBUT-side during ES operation (between −3 and 0 V, preferably between −0.8 and 0 V) (FIG. 9c). FIGS. 9d and 9e present photographs of experimental setup for the organic bioelectronic HD device (with a two-electrode device system); it was connected through a peristaltic pump that controlled the flow rates of the PBUT- and PBS-side buffers; all reservoirs were maintained in a water bath at 37° C. To confirm that the ES potential would not result in a sharp decrease in cell viability, the present invention conducted a trypan blue dye exclusion assay to evaluate the system's biocompatibility for THP1 leukemia cells (a type of white blood cell line) during 4 h of simulated dialysis treatment. The cell viability test results confirmed that this demonstration of CNF1-based HD devices, under 4 h of ES operation (CV sweeping between −3 and +3V, preferably between −0.8 and +0.8 V at a scan rate of 100 mV s$^{-1}$), could preserve the good biocompatibility, with cell viability of greater than 90% (FIG. 9f).

It should be noted that the dialysis membrane is conventional and further comprises cellulose triacetate (CTA) membrane, ethylene vinyl alcohol (EVAL) membrane, polyacrylonitrile (PAN) membrane, polyester polymer alloy (PEPA) membrane, polymethylmethacrylate (PMMA) membrane, polysulfone (PS) membrane, a regenerated cellulose (RC) membrane, or a cellulose diacetate (CDA) membrane, besides PES membrane.

It also should be noted that CE and RE are conventional and further comprises silver (Ag) electrode, gold (Au) electrode, platinum (Pt) electrode, iridium (Ir) electrode, Pt/Ir alloy electrode, iridium oxide electrode, titanium (Ti) electrode, or titanium nitride (TiN) electrode, besides Ag/AgCl electrode.

Figure 10:
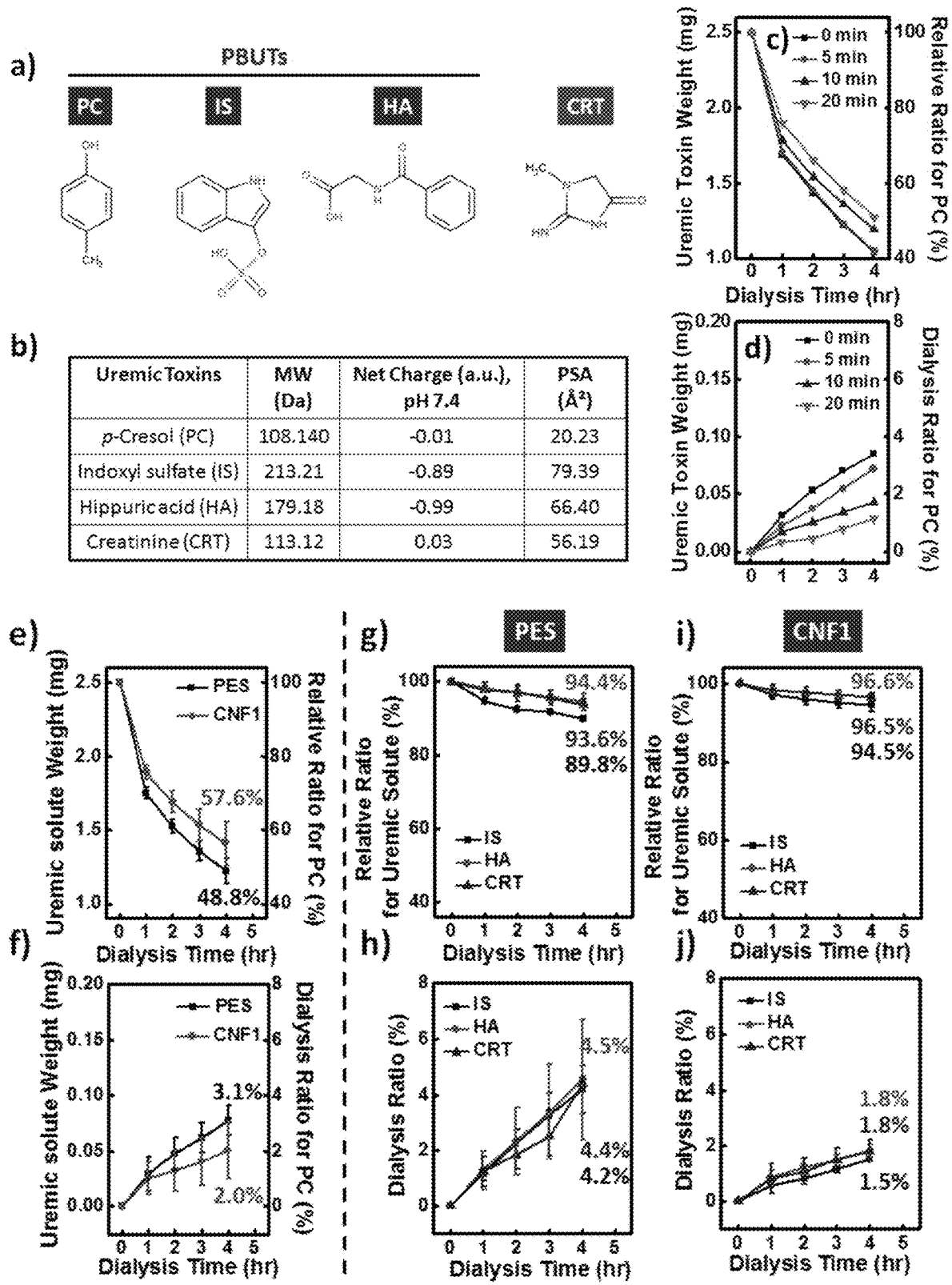
FIG. 10 (a) Chemical structures, (b) physicochemical properties of the uremic toxins PC, IS, UA, and CRT; MW, molecular weight; PSA, polar surface area, (c) removal efficiency, and (d) dialysis efficiency for the removal of PC uremic toxins using CNF1-based HD devices prepared with various electrospinning times (t=0, 5, 10, 20 min); (e) Removal efficiency and (f) dialysis efficiency for the removal of PC using various HD devices; (g,i) Removal efficiency and (h,j) dialysis efficiency for the removal of IS, HA, and CRT using (g,h) PES-based HD devices and (i,j) CNF1-based HD devices.

To examine the true impact on HD applications when using the CNF1 mats, the present invention developed a novel organic BEI electronic system as the single-membrane HD device to further study the clearance rate of four different uremic toxins: three kinds of PBUTs (PC, IS, HA) and one kind of small-molecule non-PBUT (CRT); the chemical structures and physicochemical properties of these uremic toxins are summarized in FIGS. 10a and 10b. The physicochemical properties of PC, IS, HA, and CRT were calculated using MarvinSketch 6.2.2 (ChemAxon Kft., Budapest, Hungary). The polar surface area (PSA), reflecting the molecular weight of uremic toxins, decreased in the order IS (79.39 Å$^2$), HA (66.40 Å$^2$), CRT (56.19 Å$^2$), and PC (20.23 Å$^2$); the net charge at pH 7.4, reflecting the different chemical structures of the uremic toxins, decreased in the order CRT (+0.03)>PC (−0.01)>IS (−0.89)>HA (−0.99)— the net charges of CRT and PC were almost zero, suggesting minimal electrostatic interactions. To optimize the CNF1-based devices for HD treatment, the present invention first explored the influence of the electrospinning time (0, 5, 20 min) of CNF1 on the dialysis performance (clearance rate and dialysis ratio) for the removal of PC uremic toxins, where the sum of "clearance rate" and "relative ratio" for the uremic toxin was 100%. In FIGS. 10c and 10d, although the PES membrane (0 min of electrospinning time) exhibited a higher removal efficiency for PC [relative ratio (48.8%) in PBUT-side; clearance rate (51.2%) in PBUT-side; dialysis ratio (3.4%) in PBS-side] than those of all the CNF1 samples, the electrically conductive CNF1 could possibly introduce an additional function: minimizing the protein binding fraction with the PBUTs, due to the elimination of electrostatic interactions between the PBUTs and proteins during ES operation. Therefore, when considering the possibility of BEI-based HD devices, 10 min of electrospinning of CNF1 could provide the optimized removal efficiency for PC [relative ratio (47.8%) in PBUT-side; clearance rate (52.2%) in PBUT-side; dialysis ratio (1.7%) in PBS-side] after dialysis for 4 h. As displayed in FIGS. 10e-g, the PES membrane and CNF1 provided a much higher clearance rate (lower uremic solute content) for PC than for IS, HA, and CRT, due to the inherently stronger adsorption capacity of PC [e.g., stronger π-π interactions, weaker negative-negative electrostatic repulsive interactions]; nevertheless, the present invention observed similar dialysis ratios (ca. 1.2-4.4%) for all of the solutes because of the small effective dialysis area of 3.3 cm$^2$.

Figure 11:
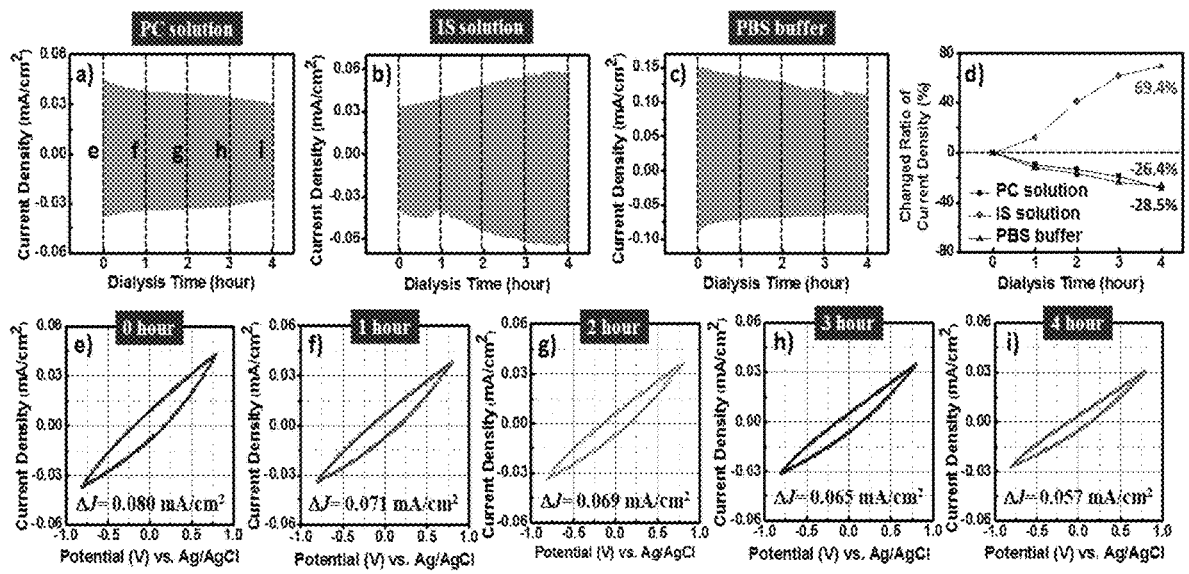
FIG. 11 (a-c) Current responses of the CNF1 device under 4 h of ES operation during repeated CV voltage sweeps from −0.8 to +0.8 V at a scan rate of 100 mV s$^{-1}$ in (a) PC solution, (b) IS solution, and (c) PBS buffer solution; (d) time-dependence of the changed ratio of current density of the CNF1 device under 4 h of ES operation in various dialysis solutions. (e-i) CV curves of the CNF1 device during ES operation; t=0, 1, 2, 3, and 4 h.

Prior to studying the ES effect on the weakening of PBUT binding to proteins, the present invention first conducted a 4-h CV sweeping to investigate the long-term stability of the CNF1-based HD devices; this stability was dependent on the reversibility of the redox behavior of CNF1 during the dialysis process (FIG. 11). FIGS. 11 a-c present the current densities during ES operation (CV sweeping between −3 and +3V, preferably between −0.8 and +0.8 V at a scan rate of 100 mV s$^{-1}$) in the as-prepared PC solution (50 ppm), IS solution (50 ppm), and PBS buffer, respectively, for CNF1-based HD devices having an effective area of 3.3 cm$^2$. In FIGS. 11a and 11e-i, the CV curves exhibit a gradual decay in the current density range (ΔJ) from 0.080 to 0.071, 0.069, 0.065, and 0.057 mA cm$^{-2}$ during ES operation from 0 to 1, 2, 3, and 4 h, respectively. There was a decreasing trend in the value of ΔJ in PBS buffer under long-term ES operation, suggesting that the changed ratio of current density appeared to decrease (−28.5% for PC treatment; −26.4% for PBS treatment) because the trapped ions within CNF1 suppressed the ionic transport (FIGS. 11a, 11c, and 11d); nevertheless, FIGS. 11b and 11d reveal that treatment with the IS solution led to an increasing trend in the value of ΔJ, suggesting that the changed ratio of current density appeared to increase from 0 to +69.4% for CNF1, possibly because of the selective removal of insulating PSS or an increase in the doping level upon treatment with the IS solution.

Figure 12:
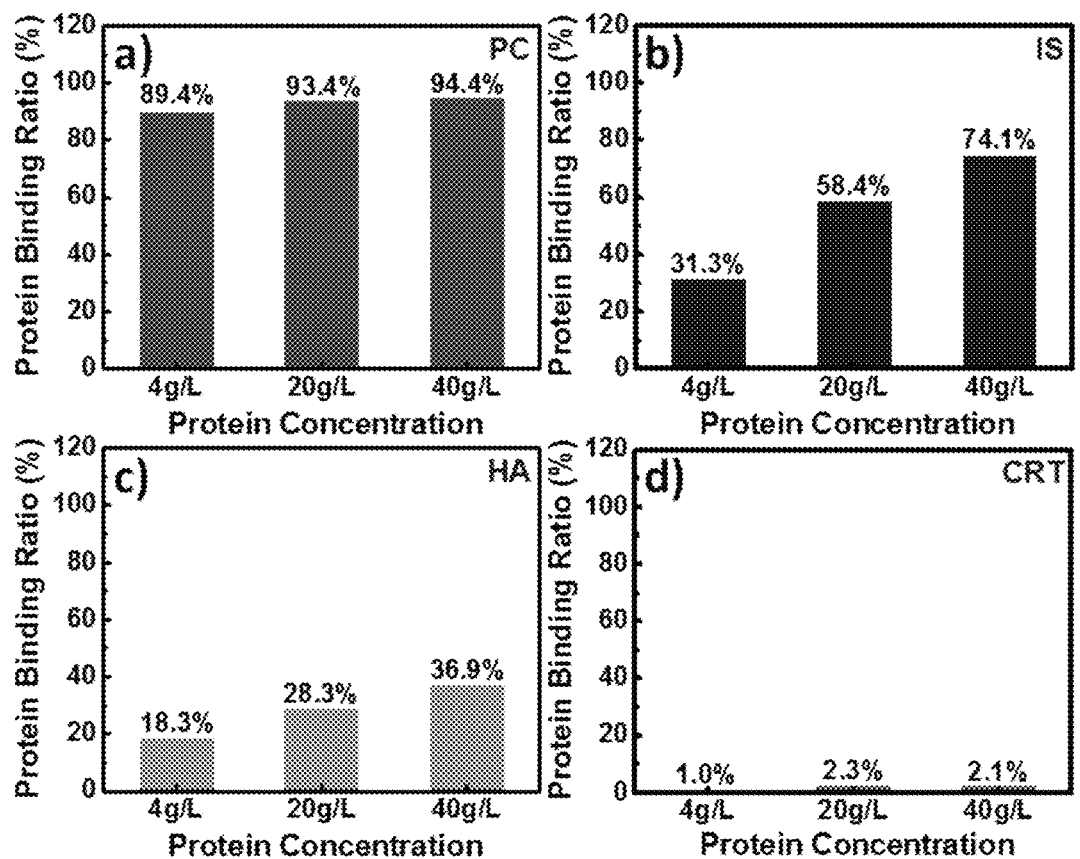
FIG. 12 Protein binding ratios of various BSA solutions (4, 20, and 40 g L$^{-1}$) preloaded with 50 ppm of the uremic toxins (a) PC, (b) IS, (c) HA, and (d) CRT.

The results reflected that the CNF1-based HD devices could provide the long-term stability of ES operation during 4 h of dialysis. Considering the normal concentration range of serum albumin (1-50 g L$^{-1}$), the present invention performed comprehensive protein binding ratio studies using 50 ppm of PC, IS, HA, and CRT uremic toxins in the presence of various amounts of BSA (4, 20, and 40 g L$^{-1}$) through centrifugal ultrafiltration (with a 30-kDa-cutoff membrane). FIG. 12 reveals that most of the CRT uremic toxin was free, meaning that the extremely low protein binding ratio of 1.0-2.1% could be attributed to the Vivaspin 2 device with a recovery performance of greater than 97.9%; nevertheless, PC was more strongly bound to BSA (estimated protein-binding ratio: 89.4-94.4%) than were IS (estimated protein-binding ratio: 31.3-74.1%) and HA (estimated protein-binding ratio: 18.3-36.9%) in the concentration range of BSA (4-40 g L$^{-1}$ in PBS buffer). Because 4 g L$^{-1}$ BSA is closer to the normal content in mimic blood (1.5 g urea, 0.04 g L$^{-1}$ lysozyme, and 1 g L$^{-1}$ BSA), the BSA solution having the concentration of 4 g L$^{-1}$ was selected for the subsequent dialysis experiments.

Figure 13:
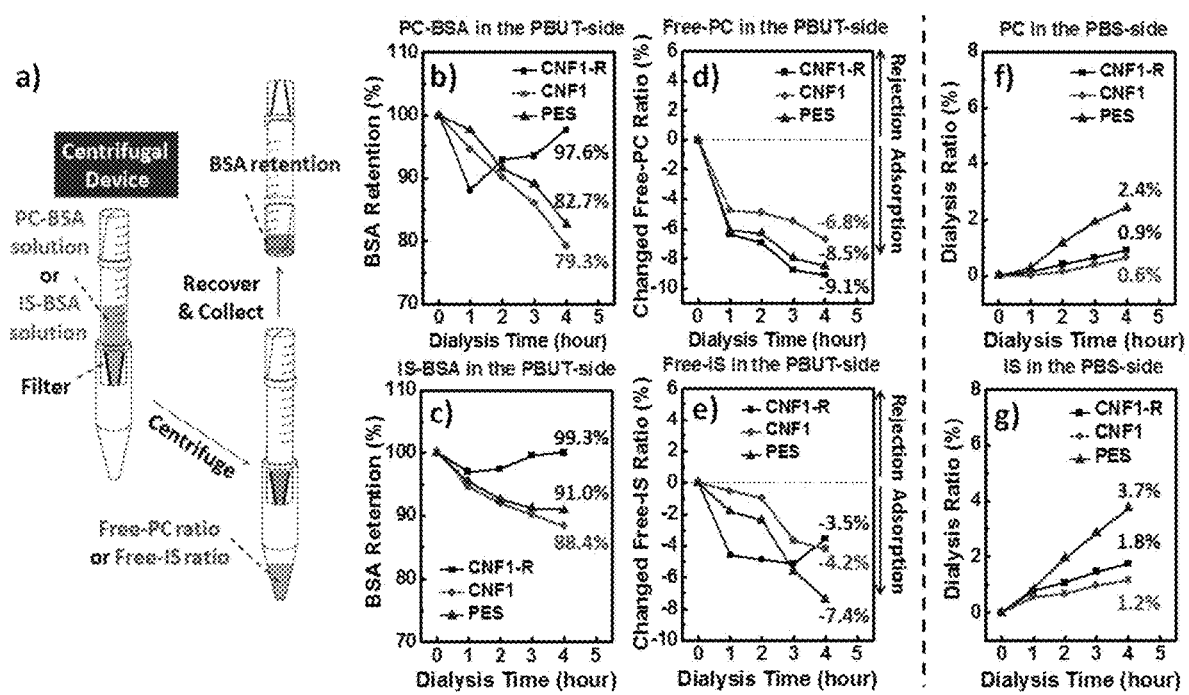
FIG. 13 (a) Procedures for collecting the target solution using a centrifugal device (Vivaspin 2, 30 kDa cutoff, GE Healthcare) and used for the detection of BSA retention and free-PBUT ratio; (b,c) BSA retention at pH 7.4, measured using different HD devices (PES, CNF1, CNF1-R) in (b) pre-bonded PC-BSA solution from PBUT-side and (c) pre-bonded IS-BSA solution from PBUT-side; (d,e) Free-PBUT ratio at pH 7.4, measured using different HD devices (PES, CNF1, CNF1-R) for (d) free-PC from PBUT-side and (e) free-IS from PBUT-side; (f,g) Dialysis ratio at pH 7.4, measured using different HD devices (PES, CNF1, CNF1-R) for (f) PC from PBS-side and (g) IS from PBS-side.

Finally, the pre-binding solution of BSA (4 g L$^{-1}$) and 50 ppm of PBUTs (e.g., PC or IS) were prepared, and then performed around 900 CV cycles (between −3 and +3V, preferably between −0.8 and +0.8 V; sweep rate: 100 mV s$^{-1}$) of ES to elucidate the BSA retention (in the PBUT-side), the change in free-PBUTs (in the PBUT-side), and the dialysis ratio (in the PBS-side) by using the CNF1-based HD device (denoted "CNF1 device") over 4 h of dialysis treatment, as compared with those measured using a PES membrane device (denoted "PES device") and CNF1 with applied ES (denoted "CNF1-R device"). As displayed in FIG. 13a, at each time point (t=0, 1, 2, 3, and 4 h) the PBUT-BSA solution was collected from the PBUT-side reservoirs during the 4 h of dialysis treatment; the sample was filled into the centrifugal column device (with 30-kDa-cutoff filter) to obtain the free-PC (or free-IS) solution from the collected PC-BSA solution (or IS-BSA solution), where the free-PC (or free-IS) ratio was estimated from the solution of the bottom column; the corresponding BSA retention was estimated by recovering and collecting the target solution from the top of column. In FIGS. 13b and 13c, the CNF1 device featured a relatively higher amount of BSA adsorption than that of the PES device, thereby resulting in relatively a lower BSA retention in the PBUT-side (79.3% for PC-BSA solution; 88.4% for IS-BSA solution) compared with that of the PES membrane (82.7% for PC-BSA solution; 91.0% for IS-BSA solution); nevertheless, no matter which PC-BSA or IS-BSA pre-binding solution was used in this demonstration, the CNF1-R device provided additional electrostatic repulsion or created an external charge disturbance between BSA and the nanofiber surface. Therefore, the degree of desorption of BSA would increase upon increasing the ES treatment time, and then it would be removed simultaneously by the axial flow streams on the PBUT-side, thereby preserving the greater BSA retention in the PBUT-side (97.6% for PC-BSA solution; 99.3% for IS-BSA solution).

Figure 14:
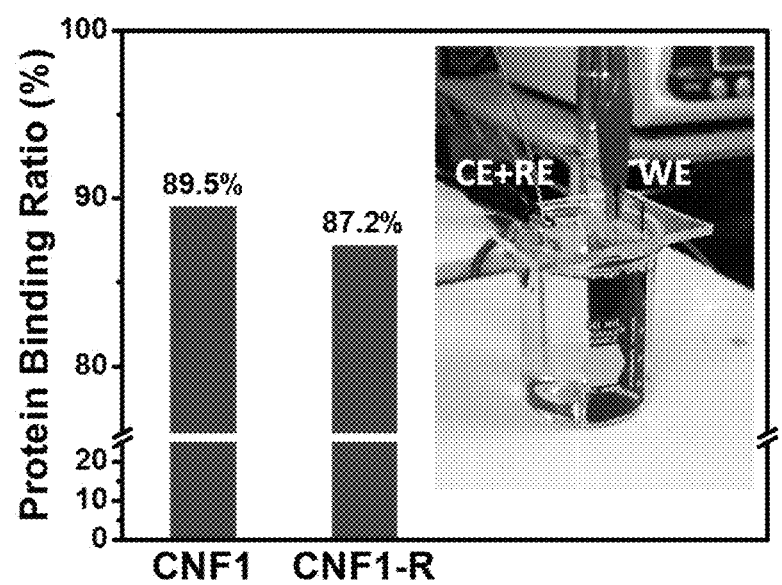
FIG. 14 Protein binding ratios determined using static CNF1 and CNF1-R device setups for the dissociation of PC and BSA. Inset: Photograph of the static CNF1-R device setup in a two-electrode configuration.

Notably, using the static CNF1 and CNF1-R device setups to study the ES effect on percentage of protein binding of the PBUTs, the present invention validated that the CNF1-R device had the ability to decrease the protein binding ratio from 89.5% for CNF1 to 87.2% (FIG. 14). For the measurement of the free-PBUT ratio from dynamic dialysis, if a rejection phenomenon occurred between free-PC and the membrane surface during the ES operation, it would result in a positive value of the changed free-PC ratio; in contrast, a negative value of the changed free-PC ratio would mean that some adsorption or dialysis phenomenon may have been playing a dominant role to simultaneously decrease the freshly free-PBUTs in this system. If the dissociated rate of PC-BSA binding was less than the clearance rate of PC, the present invention would also observe a decreasing trend in the negative value of the changed free-PC ratio. For example, the CNF1-R device exhibited a greater decreasing trend in the free-PC ratio (−9.1%) than did the CNF1 and PES devices (−6.8 and −8.5%, respectively), due to greater adsorption phenomena of free-PC on the MWCNT/PEDOT:PSS filter surface or a higher dialysis ratio on the PBS-side (FIG. 13d). In stark contrast, the CNF1-R device exhibited a smaller changed free-IS ratio (−3.5%) than did the others (−4.2% for CNF1; −7.4% for PES), due to greater electrostatic repulsive interactions occurring on the filter surface during the ES operation (FIG. 13e). These findings are consistent with the clearance rates and physicochemical properties of the uremic toxins (FIGS. 10e-g and FIG. 10b, respectively), suggesting that the CNF1 device could provide a much higher clearance rate (42.4%) for PC than for IS (3.4%), due to stronger $\pi$-$\pi$ interactions and weaker negative-negative electrostatic repulsive interactions between PC and the surface. As displayed in FIGS. 13f and 13g, when analyzing the dialysis ratios of the PBUTs through the various dialysis devices, although the PES device exhibited higher dialysis ratios (2.4% for PC; 3.7% for IS) than all the others, the results hint at the possibility that the enhancement in the dialysis rate (from 0.6 to 0.9% for the PC dialysis ratio; from 1.2 to 1.8% for the IS dialysis ratio) was due to the efficient increase in the free fraction of PBUTs when using the CNF1-R device (having a small effective area of merely 3.3 cm$^2$) under ES operation. This result was highly reproducible. Notably, an advantageous feature of the CNF1-based HD device is that it can be connected in series (for the PBUT-side) to the front of a conventional artificial kidney and provide electrically triggered dissociation of protein binding to PBUTs, thereby making up for the deficiency in performance in between.

CONCLUSION

The present invention have developed electrically conductive MWCNT/PEDOT:PSS nanofiber mats on PES dialysis membranes as BEI-based HD devices for effective removal of PBUTs from dialysis fluids through electrically triggered dissociation of protein—PBUT binding. The MWCNT/PEDOT:PSS nanofiber mats, prepared from a series of quaternary blend solutions having different component mixtures (MWCNT, PEDOT:PSS, PEO, GOPS), were fabricated through needle-type electrospinning and then investigated format the levels of both material design and device engineering. These MWCNT/PEDOT:PSS composite nanofibers possessed long-term water-resistance and high adhesion strengths on the PES dialysis membrane, due to the GOPS acting as a thermal crosslinker and adhesion promoter, respectively. The addition of MWCNTs in the PEDOT:PSS nanofibers led to MWCNT/PEDOT:PSS composite nanofibers that featured enhanced electrical conductivity and electrochemical properties, thereby promoting effective ES operation in BEI devices. The MWCNT/PEDOT:PSS nanofiber mats displayed high blood compatibility, as characterized by good anticoagulant ability, low platelet adhesion/dendrite formation, and negligible hemolysis to RBCs. The optimized CNF1 nanofiber mats functioned as novel single-membrane HD devices for studies of the removal efficiencies of three kinds of PBUTs (PC, IS, and HA) and one kind of non-PBUT (CRT), and also allowed investigations of the effect of ES on their binding with the protein BSA. Most importantly, these results confirmed that, under ES operation, CNF1-R devices can not only provide a high removal rate of PC with long-term stability but also exhibit high BSA retention after 4 h of simulated dialysis; therefore, they have potential for use in HD applications when developing next-generation bioelectronic medicines. To obtain more powerful HD treatment platforms for greater overall dialysis performance, in future applications these CNF1-R devices can be designed for concurrent setup connected in series with conventional artificial kidney devices and, thereby, enhance the blood-regeneration performance for the removal of most uremic toxins. It should be noted that the removal of PBUTs is merely an exemplary description in the embodiment of the present invention, and all protein-bound substances should be removed by the powerful HD treatment platforms of the present invention.

It will be understood that the above description of embodiments is given by way of example only and that various modifications may be made by those with ordinary skill in the art. The above specification, examples, and data provide a complete description of the present invention and use of exemplary embodiments of the invention. Although various embodiments of the invention have been described above with a certain degree of particularity, or with reference to one or more individual embodiments, those with ordinary skill in the art could make numerous alterations or modifications to the disclosed embodiments without departing from the spirit or scope of this invention.

What is claimed is:

1. A method of removing protein-bound substances by an electrically conductive polymer, comprising:
    (a) providing a (3-glycidyloxypropyl)trimethoxysilane: polystyrenesulfonate (PEDOT:PSS) solution including carbon nanotubes and a crosslinking agent;
    (b) blending the PEDOT:PSS solution with an additive solution to acquire a quaternary blend solution;
    (c) electrospinning the quaternary blend solution to form the electrically conductive polymer;
    (d) using a first electrode and the electrically conductive polymer as a second electrode to coat on a dialysis membrane to acquire a bioelectronic interface device;
    (e) introducing a biological fluid sample to the bioelectronic interface device; and
    (f) providing an electrical stimulation to reduce binding rate between proteins and the protein-bound substances,
    wherein the additive solution is ranged 5~30 wt % based on a total weight of the quaternary blend solution,
    wherein the additive solution comprises polyethylene oxide (PEO) solution, polyvinyl alcohol (PVA) solution, polyethyleneimine (PEI) solution, poly(acrylic acid) (PAA) solution, poly(styrenesulfonate) (PSS) solution, polyvinylpyrrolidone (PVP) solution, polyacrylamide (PAM) solution, poly(ethyl exazoline) solution, poly-lysine solution, poly(propylene oxide)-poly (ethylene oxide)-poly(propylene oxide) (PPO-PEO-PPO) triblock copolymers solution, poly(ethylene oxide)-poly(propylene oxide)-poly(ethylene oxide) (PEO-PPO-PEO) triblock copolymer solution, an alginate solution, hyaluronic acid (HA) solution, a gelatin solution, a collagen solution, polyglutamic acid (PGA) solution, a chitin solution, a chitosan solution, a cellulose solution or a combination thereof.

2. The method of claim 1, wherein a ratio of PEDOT and PSS is 1:2.5~1:6, and the carbon nanotubes are ranged 1~3 wt % based on total weight of the PEDOT:PSS solution.

3. The method of claim 2, wherein the (3-glycidyloxypropyl)trimethoxysilane is ranged 1~10 wt % based on total weight of the PEDOT:PSS solution.

4. The method of claim 1, wherein the crosslinking agent is (3-glycidyloxypropyl)trimethoxy silane.

5. The method of claim 1, further comprising thermal treatment of the electrically conductive polymer after the step (c).

6. The method of claim 5, wherein the thermal treatment is carried out under 80~150° C.

7. The method of claim 1, wherein the dialysis membrane comprises a polyethersulfone (PES) membrane, a cellulose triacetate (CTA) membrane, an ethylene vinyl alcohol (EVAL) membrane, a polyacrylonitrile (PAN) membrane, a polyester polymer alloy (PEPA) membrane, a polymethylmethacrylate (PMMA) membrane, a polysulfone (PS) membrane, a regenerated cellulose (RC) membrane, or a cellulose diacetate (CDA) membrane.

8. The method of claim 1, wherein the first electrode is a counter electrode or a working electrode.

9. The method of claim 8, wherein when the first electrode is the counter electrode, the second electrode is the working electrode; when the first electrode is working electrode, the second electrode is the counter electrode.

10. The method of claim 1, wherein the first electrode comprises an Ag/AgCl electrode, a silver (Ag) electrode, a gold (Au) electrode, a platinum (Pt) electrode, an iridium (Ir) electrode, a Pt/Ir alloy electrode, an iridium oxide electrode, a titanium (Ti) electrode, or a titanium nitride (TiN) electrode.

11. The method of claim 1, wherein the bioelectronic interface device comprises a reference electrode coated on the dialysis membrane.

12. The method of claim 11, wherein the reference electrode comprises an Ag/AgCl electrode, a silver (Ag) electrode, a gold (Au) electrode, a platinum (Pt) electrode, an iridium (Ir) electrode, a Pt/Ir alloy electrode, an iridium oxide electrode, a titanium (Ti) electrode, or a titanium nitride (TiN) electrode.

13. The method of claim 1, wherein the electrical stimulation comprises a cyclic voltammetric sweep.

14. The method of claim 13, wherein a potential signal of the cyclic voltammetric sweep is within a voltage range from −3 to +3 V.

15. The method of claim 1, wherein the electrical stimulation increases retention of the protein.

16. The method of claim 1, wherein the electrical stimulation increases adsorption amount or dialysis efficiency of the protein-bound substances.

17. The method of claim 1, wherein the proteins dissociates from the bioelectronic interface device after the step (f).

* * * * *